(12) United States Patent
Silverman et al.

(10) Patent No.: US 9,150,534 B2
(45) Date of Patent: Oct. 6, 2015

(54) **PRODRUGS OF FLUORINATED MEVALONATES TO INHIBIT THE MEVALONATE PATHWAY OF *STREPTOCOCCUS PNEUMONIAE***

(71) Applicants: Northwestern University, Evanston, IL (US); Albert Einstein College of Medicine of Yeshiva University, Bronx, NY (US)

(72) Inventors: Richard B. Silverman, Winnetka, IL (US); Mizuki Watanabe, Kyoto (JP); Soosung Kang, Wilmette, IL (US); Thomas S. Leyh, Katonah, NY (US)

(73) Assignees: Northwestern University, Evanston, IL (US); Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 13/780,929

(22) Filed: Feb. 28, 2013

(65) Prior Publication Data

US 2013/0245284 A1    Sep. 19, 2013

Related U.S. Application Data

(60) Provisional application No. 61/604,261, filed on Feb. 28, 2012.

(51) Int. Cl.
C07D 321/00    (2006.01)
C07D 309/30    (2006.01)
C07D 319/06    (2006.01)
C07C 69/675    (2006.01)
C07C 235/06    (2006.01)

(52) U.S. Cl.
CPC ............ *C07D 319/06* (2013.01); *C07C 69/675* (2013.01); *C07C 235/06* (2013.01); *C07D 309/30* (2013.01)

(58) Field of Classification Search
CPC .. C07D 319/06; C07D 309/30; C07C 69/675; C07C 235/06
USPC .................................................. 549/228, 292
See application file for complete search history.

(56) References Cited

FOREIGN PATENT DOCUMENTS

| EP | 1555021 | 7/2005 |
|---|---|---|
| WO | 2005053681 | 6/2005 |
| WO | 2008108834 | 9/2008 |

OTHER PUBLICATIONS

Ando et al, DFT calculations of photoabsorption spectra for alicyclic and heterocyclic compounds in the VUV region, 2003, Journal of Photopolymer Science and Technology, 16(4), pp. 537-544.*

Quistad et al, Preparation and Biological Activity of Potential Inhibitors of Insect Juvenile Hormone Biosynthesis, 1982, Journal of Agricultural Food Chemistry, 30, pp. 1151-1154.*

(Continued)

*Primary Examiner* — T. Victor Oh
(74) *Attorney, Agent, or Firm* — Reinhart Boerner Van Deuren s.c.

(57) ABSTRACT

Fluorinated prodrug compounds as can be used for selective streptococcal mevalonate pathway inhibition.

23 Claims, 5 Drawing Sheets

*Cyclic carbonate analogues*

X = O, N
R₁ = Me, CH₂F, CHF₂, CF₃
R₂ = Me, Et, Ph, 4-F-Ph, Bn, PhEt, etc.

*Cyclic acetal/ketal analogues*

X = O, N
R1 = Me, CH₂F, CHF₂, CF₃
R2 = Me, Et, Ph, 4-F-Ph, Bn, PhEt,
R3, R4 = H, Me, Et, Ph

*Ester analogues*

X = O, N
R₁ = Me, CH₂F, CHF₂, CF₃
R₂ = Me, Et, CH₂CF₃, pentafluoroBn, PhEt
R₃, R₄ = Ac, Propionyl, etc.

*Lactone analogues*

R₁ = Me, CH₂F, CHF₂, CF₃
R₂ = Ac, Propionyl, etc.

(56) References Cited

OTHER PUBLICATIONS

Shuto et al, Synthesis of two optical isomers of the insect anti-juvenile hormone agent fluromevalonolactone (FMev) and their biological activities, 1988, Agricultural and Biological Chemistry, 52(4), pp. 915-919 (three pages of abstract).*

Kondratov et al, New Synthetic approach to mevalonate and mevaldate fluoroanalogues, 2007, Tetrahedron Asymmetry, 18, pp. 1918-1925.*

PCT International Search Report from PCT/US2013/028298 dated Sep. 2, 2013.

* cited by examiner (Prior Art)

*Cyclic carbonate analogues*

X = O, N
R₁ = Me, CH₂F, CHF₂, CF₃
R₂ = Me, Et, Ph, 4-F-Ph, Bn, PhEt, etc.

*Cyclic acetal/ketal analogues*

X = O, N
R1 = Me, CH₂F, CHF₂, CF₃
R2 = Me, Et. Ph, 4-F-Ph, Bn, PhEt,
R3, R4 = H, Me, Et, Ph

*Ester analogues*

X = O, N
R₁ = Me, CH₂F, CHF₂, CF₃
R₂ = Me, Et, CH₂CF₃, pentafluoroBn, PhEt
R₃, R₄ = Ac, Propionyl, etc.

*Lactone analogues*

R₁ = Me, CH₂F, CHF₂, CF₃
R₂ = Ac, Propionyl, etc.

Cyclic carbonate analogues

X = O, S, N
R₁ = CH₂F, CHF₂, CF₃
R₂ = Me, Et, Ph, 4-F-Ph, Bn, PhEt,
    alkyl, aryl, arylalkyl, etc.

Cyclic acetal/ketal analogues

X = O, S, N
R₁ = CH₂F, CHF₂, CF₃
R₂ = Me, Et, Ph, 4-F-Ph, Bn, PhEt, alkyl, aryl,
    arylalkyl, etc.
R₃, R₄ = H, Me, Et, Ph, alkoxymethyl, etc.

Figure 4, continued
*Ester analogues*
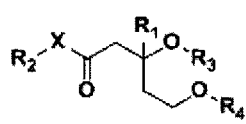
X = O, S, N
$R_1$ = $CH_2F$, $CHF_2$, $CF_3$
$R_2$ = Me, Et, $CH_2CF_3$, PhEt, alkyl, aryl, arylalkyl, etc.
$R_3$, $R_4$ = Ac, Propionyl, alkoxymethyl, etc.
*Lactone analogues*
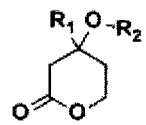
$R_1$ = $CH_2F$, $CHF_2$, $CF_3$
$R_2$ = Ac, Propionyl, alkoxymethyl, etc.
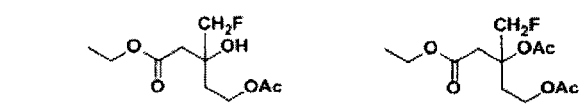
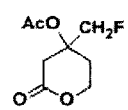
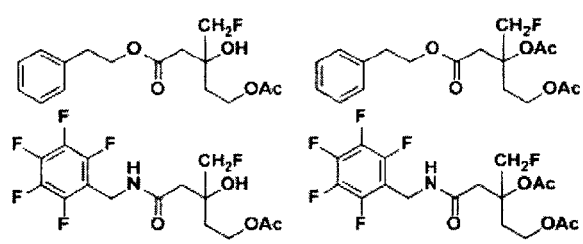
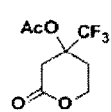
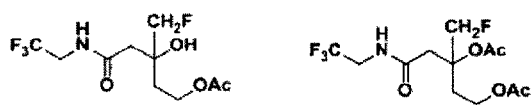
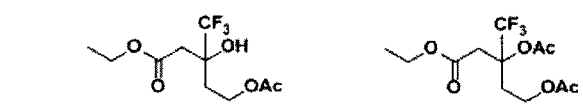
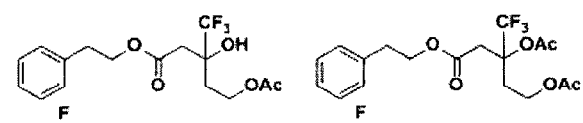
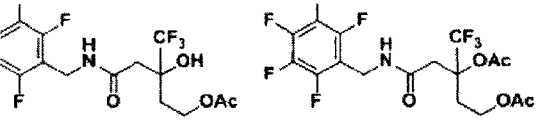
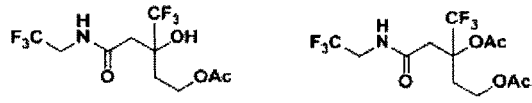

PRODRUGS OF FLUORINATED MEVALONATES TO INHIBIT THE MEVALONATE PATHWAY OF STREPTOCOCCUS PNEUMONIAE

This application claims priority benefit from application Ser. No. 61/604,261 filed Feb. 28, 2012—the entirety of which is incorporated herein by reference.

This invention was made with government support under grant number RO1 AI068989 awarded by the National Institutes of Health. The government has certain rights in the invention.

BACKGROUND OF THE INVENTION

*Streptococcus pneumoniae* is a common bacterium that causes many types of infection other than pneumonia, including acute sinusitis, otitis media, and meningitis. Infection by this bacterium is a significant cause of infant mortality in developing countries, killing more than 3000 people per day, the majority of whom are children below the age of five. Unfortunately, the incidence of strains resistant to penicillin and other antimicrobial agents has been increasing rapidly worldwide since the mid-1990s. Thus, developments of new antibiotics are needed to maintain control of this deadly organism.

The mevalonate pathway (FIG. 1) is an important cellular metabolic pathway present in all higher eukaryotes and many bacteria. Isopentenyl diphosphate, the pathway end-product, is the five-carbon building block used for the biosynthesis of isoprenoids, which in turn lead to many biologically active small molecules, including cholesterol, steroid hormones, and vitamin A. It was discovered that the mevalonate pathway in *S. pneumoniae* is regulated by 5-diphosphomevalonate (DPM). (See, Leyh, T. S., et al., *Biochemistry* 2004, 43, 16461.) DPM is a feedback inhibitor of mevalonate kinase (MVK), the first enzyme in the mevalonate pathway, binding tightly to an allosteric site of MVK in *S. pneumonia*. However, human MVK is not inhibited at DPM concentrations that essentially completely inhibit the streptococcal system. It has also been reported that *S. pneumoniae* in which the mevalonate pathway is mutated do not survive in mouse lung or serum.

On these bases, it appeared that DPM could be a lead compound for the development of new anti-streptococcal antibiotics that do not interfere with human metabolism. However, the highly-charged diphosphate compounds do not penetrate the cell membrane. Further, phosphatase degradation of the diphosphate also can occur. For these and other reasons, there remains an ongoing search in the art for effective inhibitors of the mevalonate pathway of *S. pneumoniae*.

SUMMARY OF THE INVENTION

In light of the foregoing, it is an object of the present invention to provide various compounds, compositions and/or methods for their use in the study and/or treatment of *Streptococcus pneumoniae*. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

As can relate to certain other embodiments, it can be an object of this invention to provide prodrugs of inhibitors of mevalonate kinase or other enzymes in the biosynthetic pathway of *S. pneumoniae*, such prodrug compounds including but not limited to compounds of the sort described herein.

As can relate to certain other embodiments, it can be another object of the present invention to provide such inhibitory/prodrug compounds, related compositions and/or methods of use in the study and/or treatment of infectious *S. pneumoniae*.

Other objects, feature, benefits and advantages of this invention will be apparent from this summary and the following descriptions of certain embodiments, and will be readily apparent to those skilled in the art having knowledge of various enzymatic pathways and mechanistic considerations, together with the design and synthesis of corresponding inhibitors. Such objects, features, benefits and advantages will be apparent from above as taken into conjunction with the accompanying examples, data, figures and all reasonable inferences to be drawn therefrom, alone or with consideration of the references incorporated herein.

In part, the present invention can be directed to a prodrug of a mevalonate pathway inhibitor compound, such a prodrug compound as can be selected from compounds of a formula

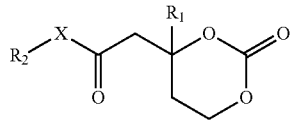

wherein X can be selected from NH, O and S; $R_1$ can be selected from fluoro-substituted methyl moieties; and $R_2$ can be selected from alkyl, fluoro-substituted alkyl, aryl, fluoro-substituted aryl, arylalkyl and fluoro-substituted arylalkyl moieties.

In certain embodiments, X can be NH or O, and/or $R_1$ can independently be either a fluoromethyl or trifluoromethyl moiety. Regardless, in certain such embodiments, $R_2$ can be an arylalkyl moiety, optionally mono- or polyfluoro-substituted. Without limitation, $R_2$ can be a mono- or di-substituted benzyl moiety.

In part, the present invention can also be directed to a prodrug of a mevalonate pathway inhibitor compound, such a prodrug compound as can be selected from compounds of a formula

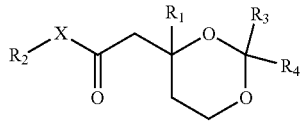

wherein X can be selected from NH, O and S; $R_1$ can be selected from fluoro-substituted methyl moieties; $R_2$ can be selected from alkyl, fluoro-substituted alkyl, aryl, fluoro-substituted aryl, arylalkyl and fluoro-substituted arylalkyl moieties; and $R_3$ and $R_4$ can be independently selected from H, alkyl, alkoxyalkyl, aryl and arylalkyl moieties.

In certain embodiments, X can be NH or O, and/or $R_1$ can independently be either a fluoromethyl or trifluoromethyl moiety. Regardless, in certain such embodiments, $R_2$ can be an arylalkyl moiety (e.g., benzyl), optionally mono- or polyfluoro-substituted (e.g., 4-fluoro- or 2,4-difluoro-). Without limitation, $R_3$ and $R_4$ can be independently selected from H and alkyl moieties. In certain such embodiments, at least one of $R_3$ and $R_4$ can be methyl.

In part, the present invention can also be directed to a prodrug of a mevalonate pathway inhibitor compound, such a prodrug compound as can be selected from compounds of a formula

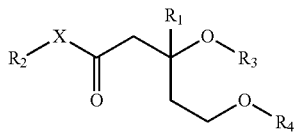

wherein X can be selected from NH, O and S; $R_1$ can be selected from fluoro-substituted methyl moieties; $R_2$ can be selected from alkyl, fluoro-substituted alkyl, aryl, fluoro-substituted aryl, arylalkyl and fluoro-substituted arylalkyl moieties; and $R_3$ and $R_4$ can be independently selected from H, acetyl, propionyl and alkoxyalkyl moieties.

In certain embodiments, X can be NH or O, and $R_1$ can be independently either a fluoromethyl or trifluoromethyl moiety. Regardless, in certain such embodiments, $R_2$ can be either an alkyl (e.g., ethyl) or arylalkyl (e.g., benzyl) moiety, each optionally mono- or polyfluoro-substituted (e.g., 1,1,1-trifluoroethyl or 1,2,3,4,5-pentafluorobenzyl). Without limitation as to either $R_1$ or $R_2$, $R_3$ and $R_4$ can be independently selected from H and acetyl moieties. In certain such embodiments, at least one of $R_3$ and $R_4$ can be acetyl.

In part, the present invention can also be directed to a prodrug of a mevalonate pathway inhibitor compound, such a prodrug compound as can be selected from compounds of a formula

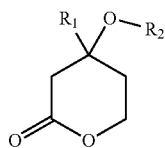

wherein $R_1$ can be selected from fluoro-substituted methyl moieties; and $R_2$ can be selected from acetyl, propionyl and alkoxyalkyl moieties.

In certain embodiments, $R_1$ can be either a fluoromethyl or trifluoromethyl moiety. Regardless, in certain such embodiments, $R_2$ can be either an acetyl or propionyl moiety. Without limitation, $R_2$ can be acetyl.

Generally, the compounds of this invention are without stereochemical limitation. As illustrated and discussed below, such compounds and/or their intermediates are available as racemic mixtures from which isomers can be resolved or are diastereomers, from which the corresponding enantiomers can be separated. Accordingly, any stereocenter can be (S) or (R) with respect to any other stereocenter(s). Further, it will be understood by those skilled in the art that any one or more the compounds of this invention can be provided as part of a pharmaceutical composition comprising a pharmaceutically-acceptable carrier component for use in conjunction with a treatment method or medicament.

In part, the present invention can also be directed to a method of treating *Streptococcus pneumoniae*. Such a method can comprise providing a compound of this invention, whether or not part of a pharmaceutical composition, and administering an effective amount of such a compound for contact with *S. pneumoniae*, mevalonate kinase and/or another enzyme expressed in the streptococcal mevalonate biosynthetic pathway. In certain such embodiments, such a compound and/or combination thereof can be present in an amount at least partially sufficient to bind or otherwise interact with an enzyme of the mevalonate pathway of such an organism, inhibit the pathway and/or inactivate the organism.

BRIEF DESCRIPTION OF THE DRAWINGS

With reference to FIG. 2, FIG. 4 provides general structures of non-limiting, representative prodrug compounds, in accordance with certain embodiments of this invention.

DETAILED DESCRIPTION OF CERTAIN EMBODIMENTS

Figure 1:
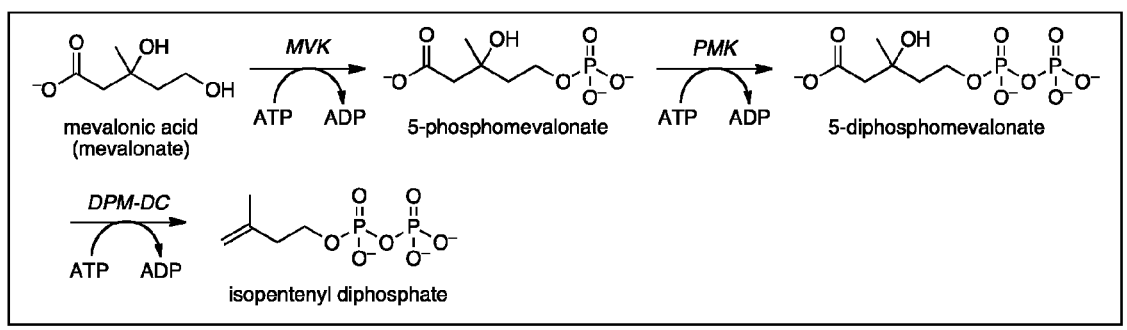
FIG. 1 illustrates the mevalonate pathway (prior art). The conversion of mevalonic acid to isopentenyl diphosphate occurs in three ATP-dependent steps catalyzed by GHMP family kinases: MVK, mevalonate kinase; PMK, phosphomevalonate kinase; DPM-DC, dephosphomevalonate decarboxylase.
Figure 2:
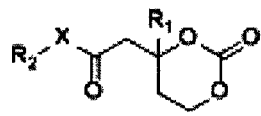
FIG. 2 provides, without limitation, prodrug compounds of diphosphomevalomate analogues, in accordance with certain embodiments of this invention.
Figure 2:
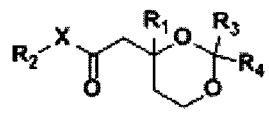
Figure 2:
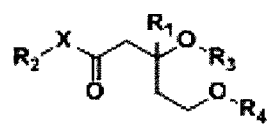
Figure 2:
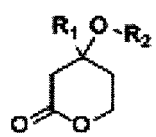

Illustrating certain non-limiting embodiments of this invention, various prodrugs of DPM analogs were designed. For instance, carbonates, acetals, ketals, amides, esters, and lactones were chosen as promoieties of the carboxyl and hydroxyl functionalities of mevalonate. Corresponding prodrug compounds, representative of this invention (see, e.g., FIG. 2), were synthesized and characterized, as discussed below.

Chemistry of Representative Carbonate Prodrugs.

A synthetic route to cyclic carbonate 4 is shown in Scheme 1. Commercially available lactone 1 was hydrolyzed under KOH basic condition, and then produced carboxylic acid 2 underwent esterification with benzyl bromide to give benzyl ester 3. Although a portion of ester 3 was converted to mevalonolactone (1) during column chromatography with silica gel, 3 was isolated as the major product. Ester 3 was treated with triphosgene to give 4 in good yields.

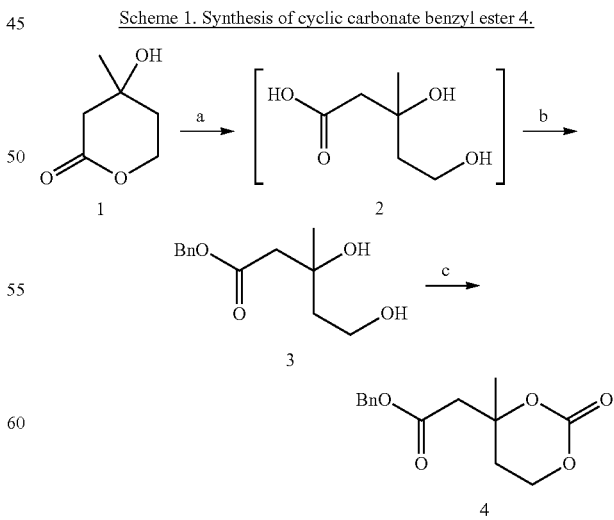

Scheme 1. Synthesis of cyclic carbonate benzyl ester 4.

(a) aq. KOH, 40° C.; aq. HCl, (b) BnBr, TBAB, THF, 50° C., 69% for 2 steps, (c) triphosgene, pyridine, 0° C., 88%

The other synthetic route to the benzyl ester (3) is shown in Scheme 2. After the hydroxyl group of 4-hydroxy-2-butanone (5) was protected with a TBS group, aldol reaction of benzyl acetate with ketone 6 was performed using LDA as a base to give 7. Desired product 3 was produced from intermediate 7 by TBS deprotection using tetrabutylammonium fluoride (TBAF) in THF.

Scheme 2. Alternative synthesis of 3.

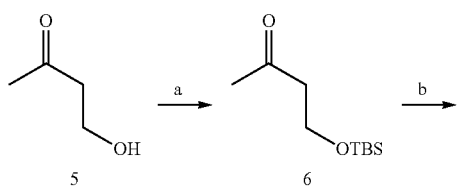

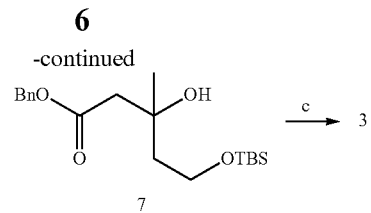

(a) TBSCl, imidazole, DMF, 90%, (b) benzyl acetate, LDA, THF, -78° C., 93%, (c) TBAF, AcOH, THF, 0° C., 72%

As shown in Scheme 3, cyclic carbonate analogues (9-16) were prepared via Pd/C catalyzed benzyl deprotection followed by coupling with diverse aryl alcohols (e.g., R=phenyl, 4-fluorophenyl, and 5-indanyl) using EDC as a coupling reagent (condition A) or with alkyl iodides (e.g., R=cyclohexyl, iPr, and tBu) using $K_2CO_3$ as a base (condition B). Carboxylic acid 8 was treated with pivaloyloxymethyl chloride and triethylamine to give the pivaloyloxymethyl ester (16, Conditions C).

Scheme 3. Synthesis of various cyclic carbonates from intermediate 4.

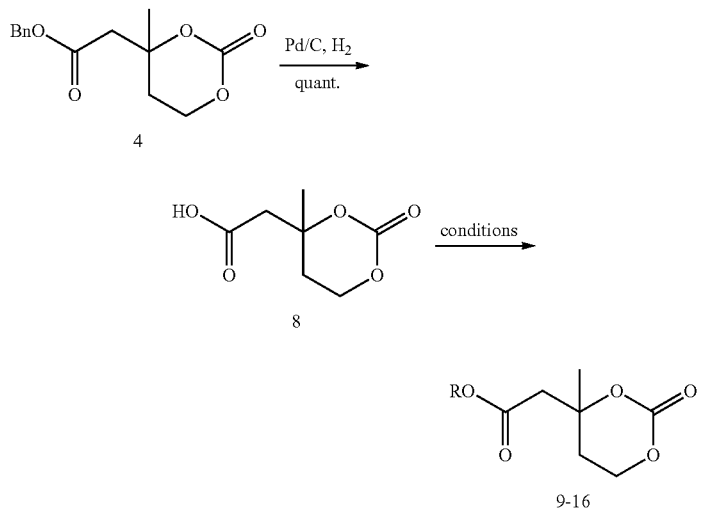

Amide analogues of cyclic carbonates were prepared from carboxylic acid 8 (Scheme 4). A coupling reaction of carboxylic acid 8 with aniline, benzyl amine, or 4-fluorobenzyl amine using HBTU as an activation reagent gave the corresponding amides (17-19) in moderate yields. (If thioalchohols (e.g., Condition A, RSH) are used in the coupling reaction, the corresponding thioesters (X=S) are produced.) Because these amides have an aromatic ring, we can monitor their stability in human plasma using HPLC with UV detector. An amide moiety would be much more stable for hydrolysis than ester moieties; thus this feature could allow investigation of the stability of the cyclic carbonate moiety in human plasma. Phenyl amide 17 was made because the N-phenylamide is chemically less stable than benzyl amide. 4-Fluorobenzyl amide 19 was also thought to be less stable than benzyl amide due to the electron withdrawing effect of fluorine on the phenyl ring.

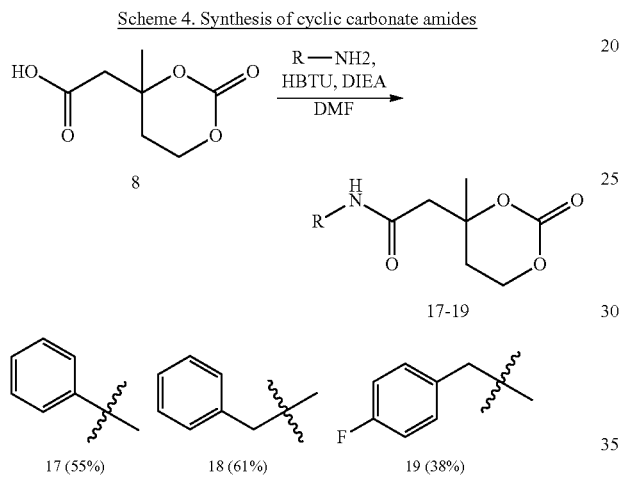

A synthetic route of 6-fluoromethyl cyclic carbonate analogues is shown in Scheme 5. Ethyl fluoroacetate (20) was treated with 1.95 equivalents of magnesium bromide at 0° C. for 30 min to give diolefin 21. Ozonolysis of crude product 21, followed by acidic treatment, gave dicarboxylic acid 22. Without purification of 22, benzylation was conducted to give diester 23 in more than 50% yield for 4 steps. When 23 was treated with DIBAL-H (3-4 equiv) at 0° C. in THF, the major product was the diol (24). Because monoester 24 underwent intramolecular cyclization on silica gel, a crude mixture of 24 was allowed to react with triphosgene without further purification to obtain desired cyclic carbonate 25 in a moderate yield. The benzyl group of 25 was removed by hydrogenation to give carboxylic acid 26. Esterification of 26 with iodomethane, iodoethane, 4-fluorobenzyl bromide, and 2,4-difluorobenzyl bromide using sodium bicarbonate as a base were carried out to give the corresponding esters (27-30), respectively.

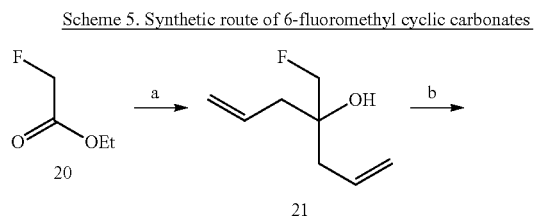

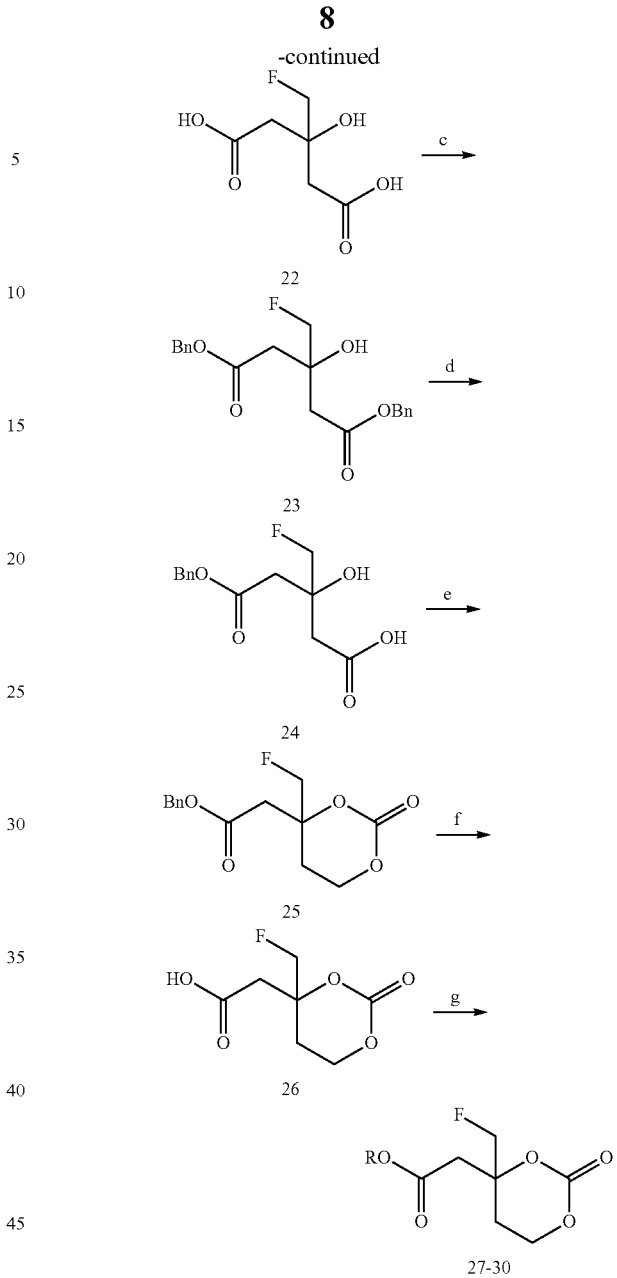

(a) allylmagnesium bromide (1.95 eq.), Et$_2$O, 0° C., < 30 min. (b) (1) ozone, CH$_2$Cl$_2$, -78° C. (2) aq. H$_2$O$_2$, AcOH, H$_2$SO$_4$, reflux, (c) BnBr, K$_2$CO$_3$, DMF, 54% for 4 steps, 69% for 2 steps, (d) DIBAL-H, THF, 0° C., (e) (Cl$_3$SO)$_2$CO, pyridine, CH$_2$Cl$_2$, 0° C., 37% for 2 steps, (f) H$_2$, Pd/C, AcOEt, 99%, (g) R—X, NaHCO$_3$, DMF, R—X, =MeI (27, 60%), R—X = EtI (28, 58%), R—X = 4-F—BnBr (29, 77%), R—X = 2,4-diF—BnBr (30, 72%), 6,6,6-Trifluoromethyl-cyclic carbonate analogues were synthesized from commercially available 4-ethoxy-1,1,1-trifluoro-3-buten-2-one (Scheme 6). The addition of benzyl acetate to enone 31 gave 32. The ethylenol was hydrolyzed to aldehyde under acidic conditions, and then produced aldehyde 33 was reduced to alcohol 34 by sodium triacetoxyborohydride. When sodium borohydride was used, the benzyl ester was also reduced to the hydroxyl group gradually. Cyclic carbonate 35 was obtained by treatment of triphosgene to the crude product (34). The benzyl group of 35 was removed by Pd/C catalyzed hydrogenation in ethyl acetate and hydrogen atmosphere. Carboxylic acid 36 was esterified with iodomethane, iodoethane, 4-fluorobenzyl bromide, or 2,4-difluorobenzyl bromide.

Scheme 6. Synthesis of 6,6,6-Trifluoromethyl-cyclic carbonate analogues

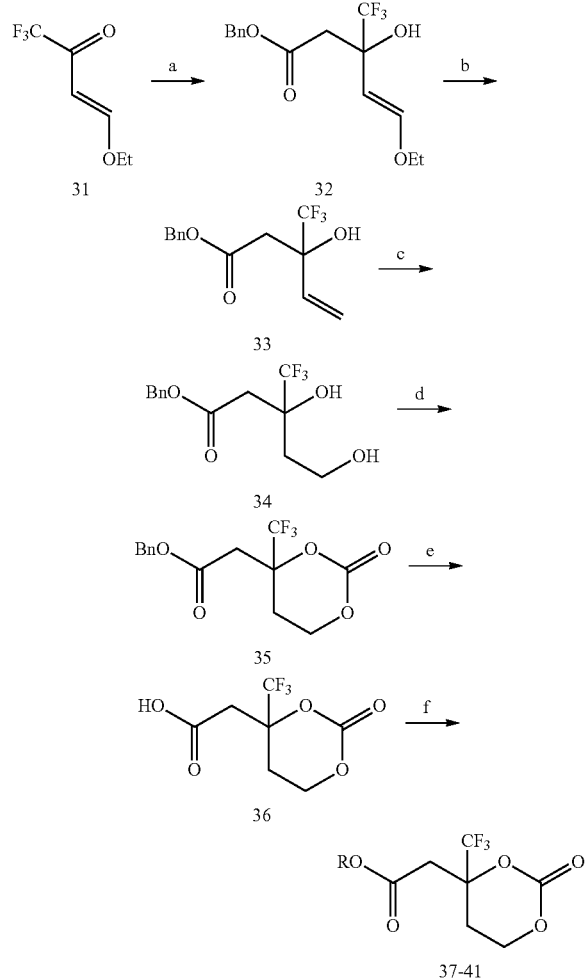

(a) benzyl acetate, LDA, THF, -78° C., 88%, (b) aq. HCl/acetone, 0° C., 80%, (c) NaBH(OAc)₃, benzene, (d) triphosgene, pyridine, CH₂Cl₂, 0° C., 68% for 2 steps, (e) H₂, Pd/C, AcOEt, 98%, (f) R—X, NaHCO₃, DMF, R—X = MeI (37, 76%), R—X = EtI (38, 71%), R—X = 4-F—BnBr (39, 88%), R—X = 2,4-diF—BnBr (40, 85%), R—X = PhEtBr (41, 75%)

Stability of the Cyclic Carbonate Prodrugs in PBS Buffer.

The stabilities of several cyclic carbonate analogues in PBS buffer (pH=7.4) were tested first to determine the standard level of the drug decomposition by media (Table 1). PBS (phosphate buffered saline) buffer is a standard solution used in plasma stability tests. The cyclic carbonate analogues (4, 25, 29, 30, 35, 39, and 40) had a UV chromophore, which allowed us to determine the amount of drug in the culture medium by HPLC analysis. After the compounds were incubated in PBS buffer at 37° C., the degradation of the compounds with incubation time was monitored. As the number of fluorines at the C6 position was increased, the half-life time ($T_{1/2}$) of the molecule was decreased dramatically (4 vs 25 vs 35). $T_{1/2}$ of the C6-methyl analogue (4) was more than 48 hours and $T_{1/2}$ of C6-monofluoromethyl analogues (25, 29, and 30) were about 25 hours while $T_{1/2}$ of C6-trifluoromethyl analogues (35, 39, and 40) were about 5 hours. If the substitution of C-6 position ($CH_3$, $CH_2F$, or $CF_3$) was same, $T_{1/2}$ of diverse benzyl esters (benzyl, 4-fluorobenzyl, or 2,4-difluorobenzyl) were not dramatically changed. These results show that the electron withdrawing effect at the C6 position affect the stability of the benzyl ester moiety. These half-lives of benzyl esters and cyclic carbonates in PBS buffer were sufficient to use these promoieties for the penetration of the cell membrane.

TABLE 1

Half-lives of diverse carbonate in PBS buffer.

| R₂ | R₁ | # | $T_{1/2}$ |
|---|---|---|---|
| Bn | CH₃ | 4 | >48 h |
| Bn | CH₂F | 25 | 25 h |
| 4-F—Bn |  | 29 | 26 h |
| 2,4-di-F—Bn |  | 30 | 22 h |
| Bn | CF₃ | 35 | 5 h |
| 4-F—Bn |  | 39 | 6 h |
| 2,4-di-F—Bn |  | 40 | 5 h |

Figure 3:
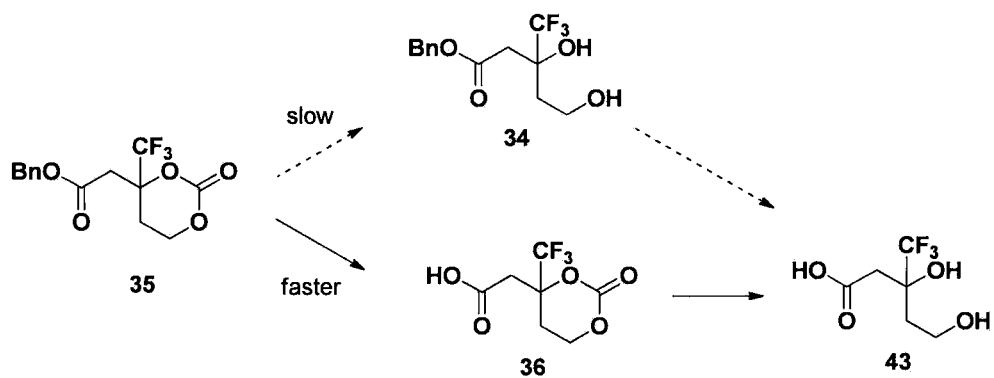
FIG. 3 provides, without limitation, a proposed decomposition mechanism for certain prodrug compounds in this invention.

Another attempts were carried out to determine whether desired decompositions occur for the trifluoromethyl analogue (35) in PBS buffer. While the peak of 35 decreased and the peak of benzyl alcohol increased in HPLC, the peak of 34 that was resulted from carbonate moiety decomposition was not observed (FIG. 3). This result shows that the cyclic carbonate moiety of 35 might be more stable than the benzyl ester moiety in PBS buffer and compound 34 might be not generated in the process of degradation of 35.

The stability of cyclic carbonate moiety in carboxylic acid 36 was tested in CD₃OD, D₂O, and PBS buffer. After 36 was incubated in PBS buffer at 37° C., solvent was removed by lyophilization, and the residue was monitored by ¹H-NMR. As a result, incubation time-dependent increase of 42 and decrease of the precursor 36 were observed. The $T_{1/2}$ of cyclic carbonate moiety of 36 in PBS buffer was about 3 h. These stability tests in PBS buffer show that the cyclic carbonate promoiety can be converted to the desired linear diol, as expected, and should be effective prodrugs upon penetration of the cell membrane.

Stability of the Cyclic Carbonate Prodrugs in Human Plasma.

The stabilities of diverse cyclic carbonate prodrugs (4, 9, 10, 11, 17, 18, 19, 25, 29, 30, 39, 40, and 41), which have a chromosphere for UV detection, in human plasma were tested using HPLC. After the mixture of test compounds and human plasma were incubated at 37° C., the degradation of the compounds was monitored by HPLC (Table 2). There were only slight differences in the half-lives depending on the ester groups; the half-life of 4 was 4 minutes and that of the other esters (9, 10, 11, 25, 29, 30, 35, 39, 40, and 41) were less than 3 minutes. As the area of the compounds decreased, the area of produced alcohols increased in HPLC for all of these compounds. The peaks of the corresponding diols (3, 24, or 34), which were the compounds that result when only the carbonate moiety of the analogues was hydrolyzed, were not observed. The half-lives of the benzyl or phenyl ester moieties may be shorter than carbonate, under tested conditions for such compounds to be used effectively as prodrugs.

The $T_{1/2}$ of N-phenyl amide 17 was also below 3 minutes. As the area of the peak of prodrug 17 decreased, the area of the peak of aniline increased. The peak of hydrolysis product of the cyclic carbonate moiety was minor compared with that of the aniline; therefore, the hydrolysis of N-phenyl amide promoiety was as fast as the ester groups.

The $T_{1/2}$ of the benzyl amide analogues (18, 19) was 8 minutes. As the area of the peaks of 18 and 19 decreased, the peaks that result only from hydrolysis of carbonate moiety increased rather than that of benzyl amine. The peak of benzyl amine was not shown even further 12-hour incubation. These results show that the benzyl amide group was stable in human plasma. If the decomposition of the cyclic carbonate moiety of 4 preceded that of the benzyl ester moiety, the half-life of 4 should be similar with that of 18. However, the half-life of 4 was half that of 18. This demonstrates that the cyclic carbonate moiety of these analogues is more stable than the benzyl ester moiety, and is consistent with the results of the stabilities in buffers. Such results suggest that the benzyl and phenyl ester moieties may not be sufficient, alone, but the cyclic carbonate moiety may be sufficiently stable in human plasma for such compounds to be useful as prodrugs.

TABLE 2

Various half-lives of diverse carbonate in human plasma.

| $R_1$ | $R_2$ | # | $T_{1/2}$ |
|---|---|---|---|
| CH₃ | Bn | 4 | 4 min |
|  | Ph | 9 | <3 min |
|  | 4-F—Ph | 10 | <3 min |
|  | 5-indanyl | 11 | <3 min |
| CH₂F | Bn | 25 | 2 min |
|  | 4-F—Bn | 29 | 2 min |
|  | 2,4-di-F—Bn | 30 | 1 min |
| CF₃ | Bn | 35 | <1 min |
|  | 4-F—Bn | 39 | <1 min |

TABLE 2-continued

Various half-lives of diverse carbonate in human plasma.

| $R_1$ | $R_2$ | # | $T_{1/2}$ |
|---|---|---|---|
|  | 2,4-di-F—Bn | 40 | <1 min |
|  | PhEt | 41 | 4 min |
| CH₃ | Ph | 17 | <3 min |
|  | Bn | 18 | 8 min |
|  | 4-F—Bn | 19 | 8 min |

Chemistry of Representative Acetal/Ketal Prodrugs.

Syntheses of acetal/ketal analogues are shown in Scheme 7. After the ring-opening reaction of 1 or 42 with benzyl amine, the introduction of the MOM group followed by treatment with $BF_3 \cdot Et_2O$, gave methylene acetals 45 and 46. The reaction of 44 and 2,2-dimethoxypropane with a catalytic amount of CSA gave acetonides 47 and 48. The treatment of 44 with benzaldehyde dimethoxy acetal and CSA in $CH_2Cl_2$ gave both diastereomers 49 and 50, in which the $CF_3$ and phenyl groups were anti and syn. These diastereomers were separated by silica gel chromatography. Compound 44 was converted to the p-methoxybenzylidene acetals (51 and 52) by treatment with anisaldehyde dimethyl acetal. These diastereomers were also separated by silica gel chromatography. In general, the p-methoxybenzylidene acetal group can undergo acid hydrolysis ten times faster than the benzylidene acetal group. So, 51 and 52 were expected to decompose more easily than 49 and 50. 2,4-dimethoxybenzylidene acetal (53) and t-butyl carbonate functionalized 54 and 55 were also prepared from intermediate 44.

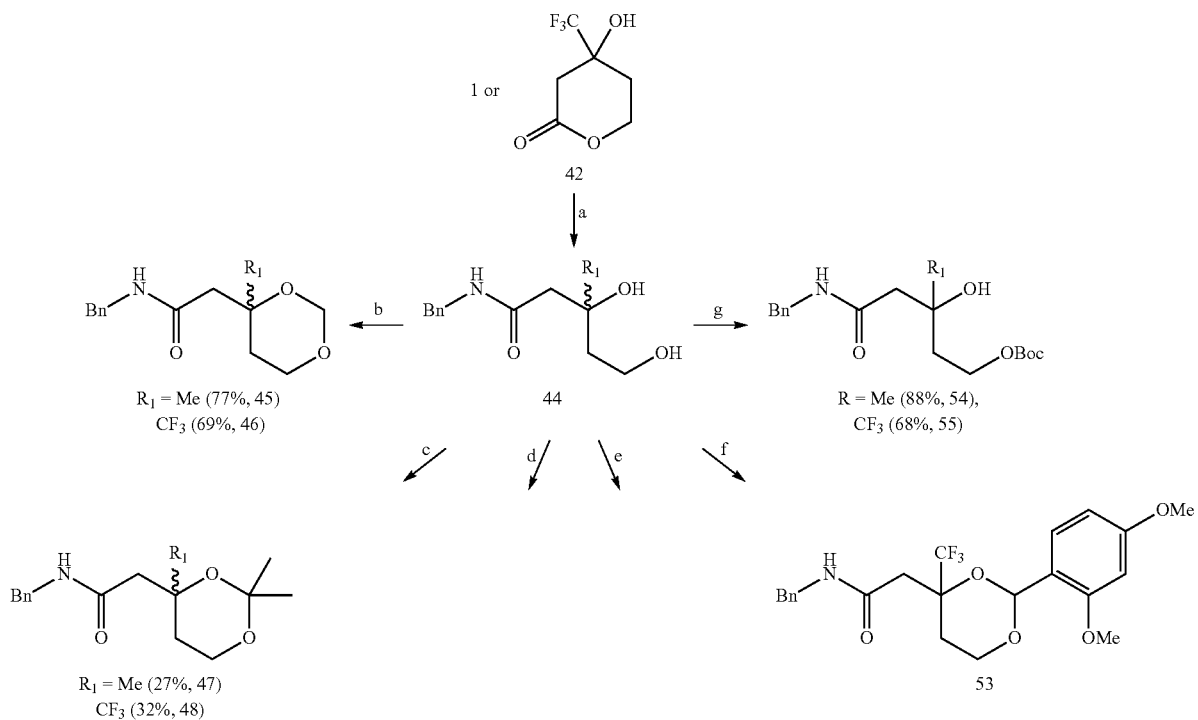

Scheme 7. Diverse acetal, ketal, and carbonate analogues.

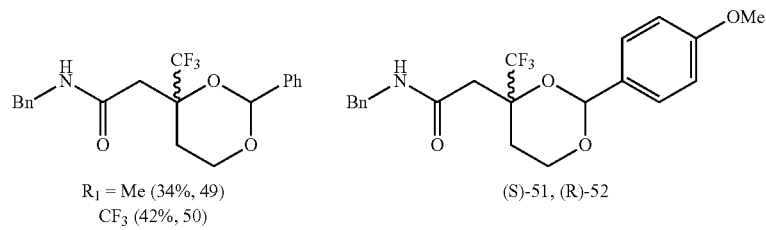

$R_1 = Me (34\%, 49)$
$CF_3 (42\%, 50)$ (S)-51, (R)-52

(a) BnNH$_2$, DMF, 80° C., 80~88%, (b) (1) MOMCl, CH$_2$Cl$_2$, 0° C. to rt, (2) BF•OEt$_2$, CH$_2$Cl$_2$, 0° C. to rt, (C) 2,2-dimethoxypropane, CSA, CH$_2$Cl$_2$, (d) benzaldehyde dimethylacetal, CSA, CH$_2$Cl$_2$, (e) anisaladehyde dimethyl acetal, CSA, CH$_2$Cl$_2$, reflux, 60%, (f) 2,4-dimethoxybenzaldehyde CSA, MS 4A, benzene, reflux, 6%, (g) Boc$_2$O, DMAP, acetonitrile, reflux Stability of the Benzyl Amide, Acetal, Ketal, and t-Butylcarbonate Promoieties in Human Plasma.

The stabilities of the benzyl amide analogues with acetal, ketal, and t-butyl carbonate promoieties (45-55) were tested in human plasma (Table 3). The half-lives in human plasma for all acetal, ketal, and t-butyl carbonate compounds were longer than 48 h. The activity of human plasma was confirmed with a compound known to undergo decomposition in human plasma.

TABLE 3

Stabilities of the benzyl amide analogues in human plasma

| $R_1$ | $R_4$ | $R_3$ | # | $T_{1/2}$ |
|---|---|---|---|---|
| CH$_3$ | H | H | 45 | >48 h |
|  | CH$_3$ | CH$_3$ | 47 | >48 h |
|  | Ph | H | 49 | >48 h |
| CF$_3$ | H | H | 46 | >48 h |
|  | CH$_3$ | CH$_3$ | 48 | >48 h |
|  | Ph | H | 50 | >48 h |
|  | 4-MeO—Ph | H | 51 | >48 h |
|  | H | 4-MeO—Ph | 52 | >48 h |
|  | 2,4-diMeO—Ph | H | 53 | >48 h |

TABLE 3-continued

Stabilities of the benzyl amide analogues in human plasma

| $R_1$ | $R_4$ | $R_3$ | # | $T_{1/2}$ |
|---|---|---|---|---|
| CH$_3$ | H | Boc | 54 | >48 h |
| CF$_3$ | H | Boc | 55 | >48 h |

Chemistry of Representative Ester Prodrugs.

Syntheses of diverse ester analogues are shown in Scheme 8 and Scheme 9. After ring-opening of 1 with various electron deficient amines, the introduction of the acetyl group gave diverse acetyl esters (57, 58, 60). The reaction of 56 with excess acetic anhydride in pyridine gave both mono- and di-acetylated products (57 and 58). The primary hydroxyl group of 59 was acetylated using one equivalent of acetic anhydride in pyridine to give 60.

C-6 fluoromethyl analogous (62, 63, 64, 65) were prepared from dibenzyl ester 23 (Scheme 9). The dibenzyl ester was reduced to triol using LiBH$_4$ and then mixed with one equivalent of acetic anhydride in pyridine to give mono-acetylated intermediate 61. That intermediate underwent oxidation using PDC and coupled with various alcohols and an amine to give corresponding products in moderate yields (62-65). (If thioalchohols are used in the coupling reaction, the corresponding thioesters (X=S) are produced.)

Scheme 8. Synthesis of diverse amide derivatives.

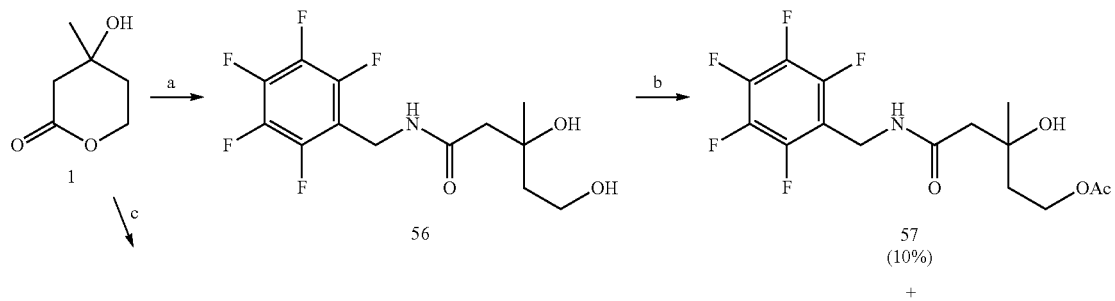

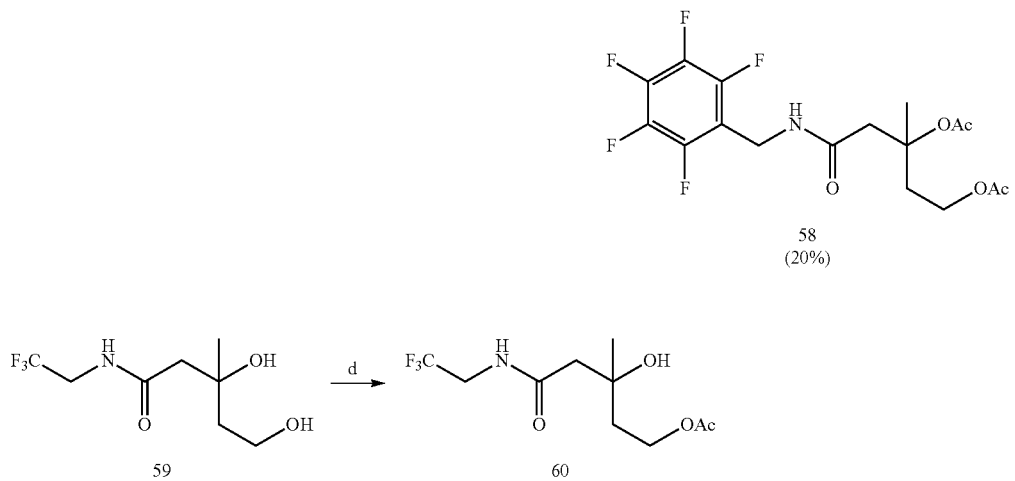

58
(20%)

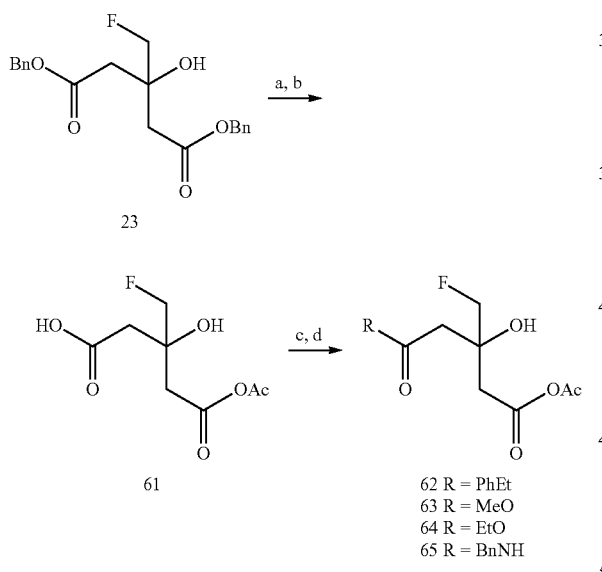

(a) 2,3,4,5,6-pentafluorobenzylamine, DMF, 80° C., 53%, (b) Ac₂O, pyridine, (c) CF₃CH₂NH₂, DMF, 80° C., 35%, (d) Ac₂O, pyridine, 39%

Scheme 9. Ester analogues of mevalonate.

(a) LiBH₄, (b) Ac₂O, DMAP, (c) PDC, (d) ROH or RNH₂, EDC, DMAP
11 ~ 25% yields.

Stability of the Ester Promoiety in Human Plasma.

The stabilities of the various amide and ester analogues (57-65) in human plasma were ascertained (Table 4). The half-life in human plasma for the amide moieties (56, 59) was greater than 2 h. Therefore, the amide bond of tested compounds is too stable in human plasma for use as a promoiety. The half-life of the acetyl groups on the alcohol of 57, 60, and 65 was about 20 minutes, suggesting that the acetyl group is a promising promoiety for the alcohols. The half-life of the ester moieties on the carboxylic acids of 62, 63 and 64 was between 10 and 22 minutes, suggesting that the ester group is a promising promoiety for the carboxylic acid.

TABLE 4

Stabilities tests of the benzyl amide analogues in human plasma.

| $R_2$ | $R_1$ | $R_3$ | $R_4$ | # | $T_{1/2}$ |
|---|---|---|---|---|---|
| pentafluorobenzyl | $CH_3$ | H | H | 56 | >120 min |
| pentafluorobenzyl | $CH_3$ | H | Ac | 57 | 20 min |
| pentafluorobenzyl | $CH_3$ | Ac | Ac | 58 | 12 min |
| $CF_3CH_2$ | $CH_2F$ | H | H | 59 | >120 min |
| $CF_3CH_2$ | $CH_2F$ | H | Ac | 60 | 20 min |
| Bn | $CH_2F$ | H | Ac | 65 | 20 min |
| PhCH₂CH₂ | $CH_3$ | H | Ac | 62 | 23 min |
| Me | $CH_2F$ | H | Ac | 63 | 10 min |
| Et | $CH_2F$ | H | Ac | 64 | 11 min |

Figure 4:
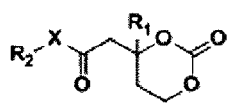
Figure 4:
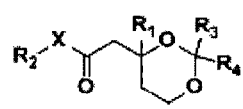
Figure 4:
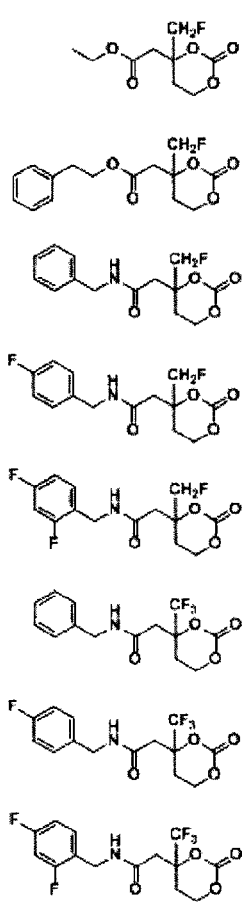
Figure 4:
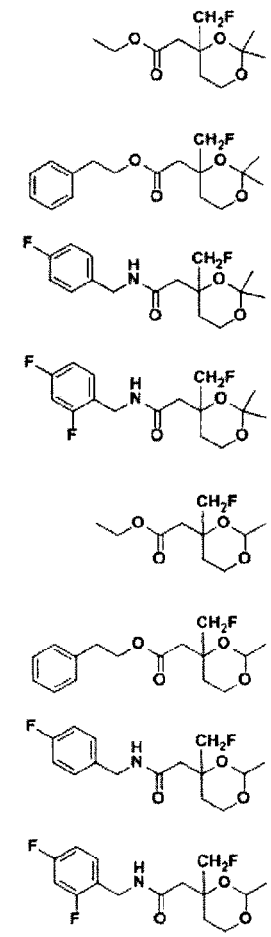

As discussed above, various studies were undertaken in the development of prodrugs of diphosphomevalonate, a feedback inhibitor of mevalonate kinase (MVK). Stability studies of diverse ester analogues of mevalonate using human plasma and PBS buffer show that it is converted to mevalonate via hydrolysis mediated by human plasma or solvent. It is also shown that the rates of decomposition of the acetates, ethyl esters, and cyclic carbonates promoieties are not only greater than that of the amides, but also of cyclic acetals and ketals in the tested analogues. In general, the ester promoiety and cyclic carbonates are converted to the desired carboxylic acid and alcohol moieties, respectively, in human plasma. Although the amides, cyclic ketals, and cyclic acetals are decomposed relatively slowly in human plasma, this study shows that the half-lives in human plasma for each functional group are controllable by modifying the electronic character of the promoiety. Plasma stability studies of these mevalonate analogues demonstrated that ester, amide, carbonate, acetal, and ketal prodrugs of fluorinated mevalonates can be used to enhance membrane permeability and oral absorption. FIG. 4 shows general and specific structures of various prodrugs of fluorinated mevalonates, in accordance with this invention.

The present invention can also, as would be understood by those skilled in the art, be extended to or include methods using or in conjunction with a pharmaceutical composition comprising a compound of the sort described herein and a physiologically or otherwise suitable formulation. In certain embodiments, the present invention includes one or more inhibitory and/or prodrug compounds, of the sort set forth above, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or nonaqueous solutions, dispersions, suspensions or emulsions. The resulting compositions can be, in conjunction with the various methods described herein, for administration or contact with *S. pneumonia*, mevalonate kinase or another enzyme expressed or otherwise present in the streptococcal mevalonate pathway. Whether or not in conjunction with a pharmaceutical composition, "contacting" means that a mevalonate kinase or other enzyme, mutation or variation thereof and one or more such inhibitor/prodrug compounds are brought together for purpose of binding and/or complexing such a compound to the enzyme. Amounts of a compound effective for inhibition may be determined empirically, and making such determinations is within the skill in the art. Inhibition or otherwise affecting mevalonate/enzyme activity includes both reduction and/or mitigation, as well as elimination of kinase activity and/or isopentenyl disphosphate and/or related intermediate production.

It is understood by those skilled in the art that dosage amount will vary with the activity of a particular compound(s), disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor/prodrug compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more anti-streptococcal mevalonate pathway inhibitor compounds for the manufacture of a medicament for therapeutic use in the treatment of human infectious diseases or the prevention thereof.

EXAMPLES OF THE INVENTION

The following non-limiting examples and data illustrate various aspects and features relating to the compounds and/or methods of the present invention, including the preparation of various prodrug compounds, as are available through the synthetic methodologies described herein. In comparison with the prior art, the present compounds provide results and data which are surprising, unexpected and contrary thereto. While the utility of this invention is illustrated through the use of several compounds and prodrug moieties which can be incorporated therein, it will be understood by those skilled in the art that comparable results are obtainable with various other prodrug compounds and/or moieties, as are commensurate with the scope of this invention.

Evaluation of Stability in PBS Buffer (pH=7.4).

The stock solution of the test compound (10 mM in acetonitrile, 50 µL) was added to PBS buffer (pH=7.4, 450 µL), and the mixture was incubated at 37° C. Aliquots of the samples were analyzed directly by HPLC (See below). These tests were conducted two times in each compound.

The other buffers that were used in the stabilities tests of 34 and 36 are following list; pH=8.2: Tris-HCl (0.1 M), pH=6.4: sodium dihydrogen phosphate (0.2 M)/sodium phosphate dibasic (0.2 M), pH=5.4: sodium phosphate dibasic (0.2 M)/citric acid (0.1 M).

Evaluation of Stability in Human Plasma.

Human plasma (100%, 480 µL) was incubated at 37° C. for 5 min. The stock solution of the test compound (100 mM in acetonitrile, 20 µL) was added to the human plasma, and the mixture was incubated at 37° C. Aliquots (80 µL) of the plasma samples were removed and mixed with an equal volume of acetonitrile. The mixture was stirred vigorously and centrifuged (5500 rpm, 5 min). The supernatant was filtered and the filtrate was analyzed by HPLC or LC-TOF (See below). These tests were conducted two times in each compound.

HPLC Analysis.

Analysis was performed on a Phenomenex® Luna C18 column (250×4.6 mm) eluted with a gradient conditions of acetonitrile and $H_2O$. Detection was by UV absorbance at 257 nm or total count of single ion in Agilent 6210 LC-TOF mass spectra.

Synthesis and Characterization

Example 1

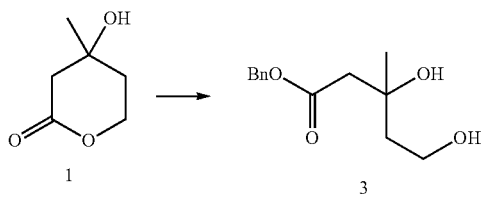

To a solution of (±)-mevalonolanctone 1 (97%, 268 mg, 2.00 mmol) in H$_2$O (4 mL) was added KOH (≥90%, 123 mg, 2.20 mmol) at rt, and the mixture was stirred at 40° C. for 1 h. The pH of the solution was lowered to about pH 7-8 (detected by pH indicator paper) with aq. HCl (0.1 M). To the mixture were added benzyl bromide (363 μL, 3.00 mmol), tetrabutylammonium bromide (967 mg, 3.00 mmol), and THF (8 mL) at rt, and the mixture was stirred at 50° C. for 4 h. After the mixture was diluted with AcOEt, the mixture was partitioned between AcOEt and brine. The organic layer was dried (Na$_2$SO$_4$) and evaporated. The residue was purified by silica gel column chromatography (50% to 75% AcOEt in hexane) to give 3 (329 mg, 69%) as a colorless oil. $^1$H NMR (500 MHz, CDCl$_3$) δ 7.33-7.38 (m, 5H, aromatic), 5.17 (s, 2H, benzyl-CH$_2$), 4.04 (br s, 1H, OH), 3.88 (m, 1H, CH$_2$CH$_2$O), 3.81 (m, 1H, CH$_2$CH$_2$O), 2.90 (br s, 1H, OH), 2.69 (d, 1H, OC(O)CH$_2$, J=15.5 Hz), 2.52 (d, 1H, OC(O)CH$_2$, J=15.5 Hz), 1.80 (m, 1H, CH$_2$CH$_2$O), 1.74 (m, 1H, CH$_2$CH$_2$O), 1.32 (s, 3H, CH$_3$); $^{13}$C NMR (125 MHz, CDCl$_3$) δ 172.7, 135.3, 128.7, 128.5, 128.4, 72.2, 66.7, 59.4, 45.1, 42.1, 26.9; HRMS (pos. ion ESI) m/z calcd for (M+Na)$^+$ C$_{13}$H$_{18}$NaO$_4$: 261.1103. Found: 261.1105.

Example 2

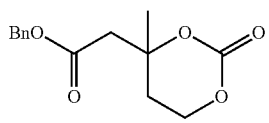

To a solution of 3 (436 mg, 1.83 mmol) in CH$_2$Cl$_2$ (15 mL) was added pyridine (224 μL, 2.75 mmol), and the mixture was stirred at 0° C. for 15 min. A solution of triphosgene (98%, 665 mg, 2.20 mmol) in CH$_2$Cl$_2$ (5 mL) was added to the mixture, and the resulting mixture was stirred at 0° C. for 30 min. The reaction was quenched with addition of sat. aq. NH$_4$Cl, and extracted with AcOEt. The organic layer was washed with brine, dried (Na$_2$SO$_4$), and evaporated. The residue was purified by silica gel column chromatography (33% to 50% AcOEt in hexane) to give 4 (425 mg, 88%) as a light yellow oil.

Example 3

To a solution of 7 (Example 5, below, 324 mg, 0.919 mmol) in THF (8 mL) were added tetrabutylammonium fluoride (1.0 M solution in THF, 1.10 mL, 1.10 mmol) and AcOH (1.0 M solution in THF, 2.20 mL, 2.20 mmol) at 0° C., and the mixture was stirred at 0° C. for 24 h. The mixture was diluted with AcOEt and washed with sat. aq. NaHCO$_3$. The organic layer was washed with brine, dried (Na$_2$SO$_4$), and evaporated. The residue was purified quickly by silica gel column chromatography (50% to 80% AcOEt in hexane) to give compound 3. After the residue was dissolved in CH$_2$Cl$_2$ (8 mL), pyridine (163 μL, 2.00 mmol) was added to the solution and the mixture was cooled at 0° C. To the mixture was added a solution of triphosgene (98%, 306 mg, 1.00 mmol) in CH$_2$Cl$_2$ (1 mL), and the resulting mixture was stirred at 0° C. for 30 min. The reaction was quenched with addition of sat. aq. NH$_4$Cl, and extracted with AcOEt. The organic layer was washed with brine, dried (Na$_2$SO$_4$), and evaporated. The residue was purified by silica gel column chromatography (33% to 50% AcOEt in hexane) to give 4 (155 mg, 64% for 2 steps) as a light yellow oil, and 7 was recovered (39 mg, 12%).

$^1$H NMR (500 MHz, CDCl$_3$) δ 7.34-7.40 (m, 5H, aromatic), 5.14 (s, 2H, benzyl-CH$_2$), 4.42 (m, 2H, CH$_2$CH$_2$O), 2.83 (s, 2H, OC(O)CH$_2$), 2.36 (m, 1H, CH$_2$CH$_2$O), 2.08 (m, 1H, CH$_2$CH$_2$O), 1.57 (s, 3H, CH$_3$); $^{13}$C NMR (125 MHz, CDCl$_3$) δ 168.7, 148.5, 135.1, 128.6, 128.5, 128.4, 81.0, 66.9, 64.5, 44.8, 30.4, 25.8; HRMS (pos. ion ESI) m/z calcd for (M+Na)$^+$ C$_{14}$H$_{16}$NaO$_5$: 287.0895. Found: 287.0899.

Example 4

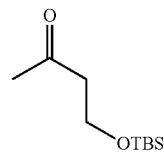

To a solution of 4-hydroxy-2-butanone (273 μL, 3.00 mmol) in DMF (20 mL) were added tert-butylchlorodimethylsilane (559 mg, 3.60 mmol) and imidazole (490 mg, 7.20 mmol) at 0° C., and the mixture was stirred at rt for 12 hr. After the addition of MeOH, the mixture was diluted with Et$_2$O and washed with H$_2$O (×3). The organic layer was washed with brine, dried (Na$_2$SO$_4$), and evaporated. The residue was purified by silica gel column chromatography (5% AcOEt in hexane) to give 6 (548 mg, 90%) as a colorless liquid. $^1$H NMR (500 MHz, CDCl$_3$) δ 3.88 (t, 2H, CH$_2$CH$_2$O, J=6.3 Hz), 2.62 (t, 2H, CH$_2$CH$_2$O, J=6.3 Hz), 2.19 (s, 3H, CH$_3$), 0.88 (s, 9H, C(CH$_3$)$_3$), 0.05 (s, 6H, Si(CH$_3$)$_2$); $^{13}$C NMR (125 MHz, CDCl$_3$) δ 208.2, 58.8, 46.5, 30.9, 25.8, 18.2, −5.5; HRMS (pos. ion ESI) m/z calcd for (M+Na)$^+$ C$_{10}$H$_{22}$NaO$_2$Si: 225.1287. Found: 225.1280.

Example 5

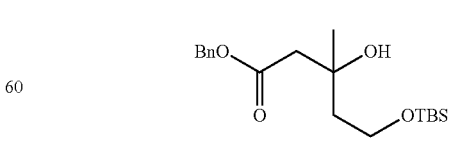

To a solution of lithium diisopropylamide (1.8 M solution in heptane/THF/ethyl benzene, 7.93 mL, 14.3 mmol) in THF (105 mL) was added benzyl acetate (2.04 mL, 14.3 mmol) at −78° C., and the mixture was stirred at −78° C. for 30 min. A solution of 6 (2.41 g, 11.9 mmol) in THF (5 mL) was added to the mixture via canule at −78° C., and the resulting mixture was stirred at −78° C. for 1 h. After addition of sat. aq. NH$_4$Cl, the mixture was warmed to room temperature, and evaporated. The residue was separated between AcOEt and sat. aq. NH$_4$Cl. The organic layer was washed with brine, dried (Na$_2$SO$_4$), and evaporated. The residue was purified by silica gel column chromatography (5% to 8% AcOEt in hexane) to give 7 (3.92 mg, 93%) as a colorless oil. $^1$H NMR (500 MHz, CDCl$_3$) δ 7.31-7.35 (m, 5H, aromatic), 5.17 (d, 1H, benzyl-CH$_2$, J=7.5 Hz), 5.12 (d, 1H, benzyl-CH$_2$, J=7.5 Hz), 4.20 (s, 1H, OH), 3.86 (t, 2H, CH$_2$CH$_2$O, J=3.6 Hz), 2.66 (d, 1H, OC(O)CH$_2$, J=15.6 Hz), 2.60 (d, 1H, OC(O)CH$_2$, J=15.6 Hz), 1.82 (m, 2H, CH$_2$CH$_2$O), 1.30 (s, 3H, CH$_3$), 0.89 (s, 9H, C(CH$_3$)$_3$), 0.07 (s, 6H, Si(CH$_3$)$_2$); HRMS (pos. ion ESI) m/z calcd for (M+Na)$^+$ C$_{19}$H$_{32}$NaO$_4$Si: 375.1968. Found: 375.1965.

Example 6

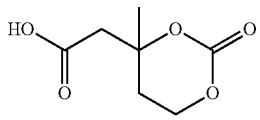

8

To a solution of 4 (340 mg, 1.29 mmol) in AcOEt (15 mL) was added Pd/C (10%, 33 mg), and the mixture was stirred under H$_2$ gas at rt for 30 min. The resulting mixture was filtered through Celite with acetone, and the filtrate was evaporated to give 8 (224 mg, quant.) as a colorless solid. $^1$H NMR (500 MHz, CD$_3$OD) δ 4.48 (m, 2H, CH$_2$CH$_2$O), 2.82 (d, 1H, OC(O)CH$_2$, J=15.5 Hz), 2.78 (d, 1H, OC(O)CH$_2$, J=15.5 Hz), 2.48 (m, 1H, CH$_2$CH$_2$O), 2.12 (m, 1H, CH$_2$CH$_2$O), 1.57 (s, 3H, CH$_3$); $^{13}$C NMR (125 MHz, CD$_3$OD) δ 172.5, 151.9, 83.3, 66.2, 45.2, 31.3, 26.1; HRMS (pos. ion ESI) m/z calcd for (M+Na)$^+$ C$_7$H$_{10}$NaO$_5$: 197.0426. Found: 197.0426. mp. 83-85° C.

Example 7

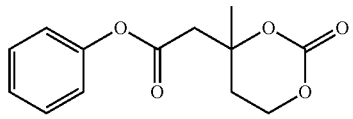

9

To a solution of 8 (35 mg, 0.20 mmol) in CH$_3$CN/CH$_2$Cl$_2$ (1/1, 1.5 mL) were added phenol (85 mg, 0.90 mmol), N-(3-dimethylaminopropyl)-N-ethylcarbodiimide hydrochloride (38 mg, 0.20 mmol), and DMAP (20 mg, 0.16 mmol) at 0° C., and the mixture was stirred at rt for 1 h. The mixture was diluted with AcOEt and partitioned between AcOEt and aq. HCl (0.5 M). The organic layer was washed with sat. aq. NaHCO$_3$, brine, dried (Na$_2$SO$_4$), and evaporated. The residue was purified by silica gel column chromatography (33% to 50% AcOEt in hexane) to give 9 (27 mg, 54%) as a white solid. $^1$H NMR (500 MHz, CDCl$_3$) δ 7.40 (t, 2H, aromatic, J=7.9, 8.0 Hz), 7.26 (t, 1H, aromatic, J=8.0 Hz), 7.09 (d, 2H, aromatic, J=7.9 Hz), 4.49 (t, 2H, CH$_2$CH$_2$O, J=5.1 Hz), 3.05 (s, 2H, OC(O)CH$_2$), 2.47 (m, 1H, CH$_2$CH$_2$O), 2.19 (m, 1H, CH$_2$CH$_2$O), 1.68 (s, 3H, CH3); $^{13}$C NMR (125 MHz, CDCl$_3$) δ 167.6, 150.0, 148.4, 129.6, 126.3, 121.3, 81.0, 64.5, 44.9, 30.6, 25.9; HRMS (pos. ion ESI) m/z calcd for (M+Na)$^+$ C$_{13}$H$_{14}$NaO$_5$: 273.0739. Found: 273.0731. mp. 62-62.5° C.

Example 8

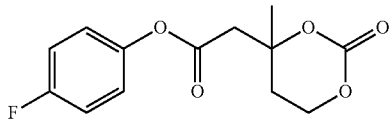

10

10 (35 mg, 65%, white solid) was prepared from 8 (35 mg, 0.20 mmol) as described for the preparation of 9 using 4-fluorophenol instead of phenol. $^1$H NMR (500 MHz, CDCl$_3$) δ 7.06-7.08 (m, 4H, aromatic), 4.48 (m, 2H, CH$_2$CH$_2$O), 3.03 (s, 2H, OC(O)CH$_2$), 2.48 (m, 1H, CH$_2$CH$_2$O), 2.17 (m, 1H, CH$_2$CH$_2$O), 1.67 (s, 3H, CH$_3$); $^{13}$C NMR (125 MHz, CDCl$_3$) δ 167.6, 160.4 (d), 148.4, 145.8, 122.8, 116.3, 80.9, 64.5, 44.9, 30.6, 25.9; HRMS (pos. ion ESI) m/z calcd for (M+Na)$^+$ C$_{13}$H$_{13}$FNaO$_5$: 291.0645. Found: 291.0648. mp. 68-69° C.

Example 9

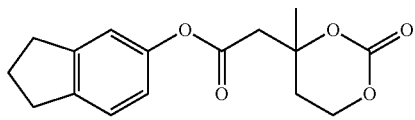

11

11 (40 mg, 70%, white solid) was prepared from 8 (35 mg, 0.20 mmol) as described for the preparation of 9 using 5-indanol instead of phenol. $^1$H NMR (500 MHz, CDCl$_3$) δ 7.21 (d, 2H, aromatic, J=8.1 Hz), 6.92 (s, 1H, aromatic), 6.81 (d, 2H, aromatic, J=8.1 Hz), 4.48 (m, 2H, CH$_2$CH$_2$O), 3.03 (s, 2H, OC(O)CH$_2$), 2.91 (m, 4H, —CH$_2$CH$_2$CH$_2$—), 2.47 (m, 1H, CH$_2$CH$_2$O), 2.19 (m, 1H, CH$_2$CH$_2$O), 2.11 (m, 2H, —CH$_2$CH$_2$CH$_2$—), 1.68 (s, 3H, CH3); $^{13}$C NMR (125 MHz, CDCl$_3$) δ 168.0, 148.4, 146.0, 142.3, 124.9, 118.8, 117.3, 81.1, 64.6, 44.9, 32.9, 32.3, 30.6, 25.9, 25.7; HRMS (pos. ion ESI) m/z calcd for (M+Na)$^+$ C$_{16}$H$_{18}$NaO$_5$: 313.1052. Found: 313.1050. mp. 88-89° C.

Example 10

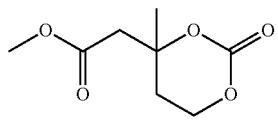

12

To a solution of 8 (130 mg, 0.746 mmol) in DMF (3 mL) were added iodomethane (140 μL, 2.24 mmol) and K$_2$CO$_3$ (309 mg, 2.24 mmol), and the mixture was stirred at rt for 12 h. The mixture was diluted with AcOEt and H$_2$O, and separated. The organic layer was washed with H$_2$O (×2) and brine, dried (Na$_2$SO$_4$), and evaporated. The residue was purified by silica gel column chromatography (50% AcOEt in hexane) to give 12 (105 mg, 75%) as a colorless oil. $^1$H NMR (500 MHz, CDCl$_3$) δ 4.44 (m, 2H, CH$_2$CH$_2$O), 3.71 (s, 3H, OCH$_3$), 2.80 (s, 2H, OC(O)CH$_2$), 2.40 (m, 1H, CH$_2$CH$_2$O), 2.13 (m, 1H, CH$_2$CH$_2$O), 1.58 (s, 3H, CH$_3$); $^{13}$C NMR (125 MHz, CDCl$_3$) δ 169.4, 148.6, 81.0, 64.6, 52.1, 44.6, 30.5, 25.8; HRMS (pos. ion ESI) m/z calcd for (M+Na)$^+$ C$_8$H$_{12}$NaO$_5$: 211.0582. Found: 211.0590.

Example 11

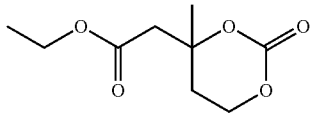

13 (99 mg, 70%, colorless oil) was prepared from 8 (132 mg, 0.758 mmol) as described for the preparation of 12 using iodoethane instead of iodomethane. $^1$H NMR (500 MHz, CDCl$_3$) δ 4.45 (t, 2H, —CH$_2$CH$_2$O—, J=6.6 Hz), 4.17 (q, 2H, CH$_3$CH$_2$O—, J=7.1 Hz), 2.79 (s, 2H, OC(O)CH$_2$), 2.40 (m, 1H, CH$_2$CH$_2$O), 2.12 (m, 1H, CH$_2$CH$_2$O), 1.58 (s, 3H, CH$_3$), 1.28 (t, 3H, CH$_3$CH$_2$O—, J=7.1 Hz); $^{13}$C NMR (125 MHz, CDCl$_3$) δ 169.0, 148.7, 81.2, 64.7, 61.3, 45.0, 30.7, 26.0, 14.2; HRMS (pos. ion ESI) m/z calcd for (M+Na)$^+$ C$_9$H$_{14}$NaO$_5$: 225.0739. Found: 225.0738.

Example 12

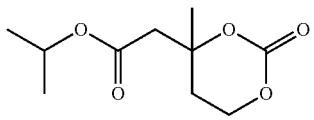

14 (21 mg, 75%, colorless oil) was prepared from 8 (23 mg, 0.13 mmol) as described for the preparation of 12 using 2-iodopropane instead of iodomethane. $^1$H NMR (500 MHz, CDCl$_3$) δ 5.03 (m, 1H, CH(CH$_3$)$_2$), 4.44 (m, 2H, CH$_2$CH$_2$O), 2.75 (s, 2H, OC(O)CH$_2$), 2.40 (m, 1H, CH$_2$CH$_2$O), 2.11 (m, 1H, CH$_2$CH$_2$O), 1.58 (s, 3H, CH$_3$), 1.26 (s, 3H, CH(CH$_3$)$_2$), 1.25 (s, 3H, CH(CH$_3$)$_2$); $^{13}$C NMR (125 MHz, CDCl$_3$) δ 168.4, 148.6, 81.1, 68.8, 64.6, 45.2, 30.5, 25.9, 21.7; HRMS (pos. ion ESI) m/z calcd for (M+Na)$^+$ C$_{10}$H$_{16}$NaO$_5$: 239.0895. Found: 239.0895.

Example 13

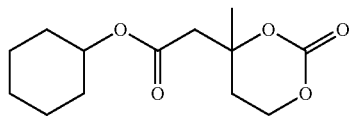

15 (4.2 mg, 13%, colorless oil) was prepared from 8 (22 mg, 0.13 mmol) as described for the preparation of 12 using iodocyclohexane instead of iodomethane. $^1$H NMR (500 MHz, CDCl$_3$) δ 4.78 (m, 1H, cyclohexyl), 4.44 (m, 2H, CH$_2$CH$_2$O), 2.79 (d, 1H, OC(O)CH$_2$, J=15.2 Hz), 2.75 (d, 1H, OC(O)CH$_2$, J=15.2 Hz), 2.40 (m, 1H, CH$_2$CH$_2$O), 2.11 (m, 1H, CH$_2$CH$_2$O), 1.85 (m, 2H, cyclohexyl), 1.73 (m, 2H, cyclohexyl), 1.58 (s, 3H, CH$_3$), 1.56 (m, 2H, cyclohexyl), 1.32-1.44 (m, 4H, cyclohexyl); $^{13}$C NMR (125 MHz, CDCl$_3$) δ 168.3, 148.6, 81.1, 73.8, 64.6, 45.2, 31.5, 30.5, 26.0, 25.2, 23.7; HRMS (pos. ion ESI) m/z calcd for (M+Na)$^+$ C$_{13}$H$_{20}$NaO$_5$: 279.1208. Found: 279.1205.

Example 14

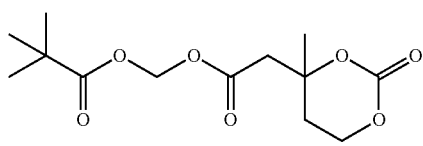

To a solution of 8 (29 mg, 0.17 mmol) in DMF (1 mL) were added chloromethyl pivalate (97%, 74 μL, 0.50 mmol), triethylamine (105 μL, 0.750 mmol) and sodium iodide (2.5 mg, 0.017 mmol), and the mixture was stirred at rt for 12 h. The mixture was diluted with AcOEt, and partitioned between AcOEt and aq. HCl (0.5 M). The organic layer was washed with sat. aq. NaHCO$_3$, H$_2$O, and brine, dried (Na$_2$SO$_4$), and evaporated. The residue was purified by silica gel column chromatography (AcOEt in hexane) to give 16 (18 mg, 38%) as a colorless oil. $^1$H NMR (500 MHz, CDCl$_3$) δ 5.77 (s, 2H, OCH$_2$O), 4.44 (m, 2H, CH$_2$CH$_2$O), 2.84 (s, 2H, OC(O)CH$_2$), 2.37 (m, 1H, CH$_2$CH$_2$O), 2.12 (m, 1H, CH$_2$CH$_2$O), 1.58 (s, 3H, CH$_3$), 1.22 (s, 9H, C(CH$_3$)$_3$); $^{13}$C NMR (125 MHz, CDCl$_3$) δ 177.1, 167.6, 148.3, 80.7, 79.7, 64.5, 44.6, 38.8, 30.5, 26.8, 25.7; HRMS (pos. ion ESI) m/z calcd for (M+Na)$^+$ C$_{13}$H$_{20}$NaO$_7$: 311.1107. Found: 311.1109.

Example 15

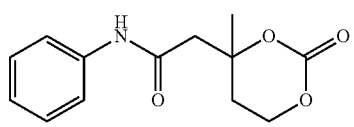

To a solution of 8 (29 mg, 0.17 mmol) in DMF (1 mL) were added aniline (45 μL, 0.50 mmol), HBTU (64 mg, 0.17 mmol), N,N-diisopropylethylamine (59 μL, 0.34 mmol) at 0° C., and the mixture was stirred at rt for 8 h. The mixture was diluted with AcOEt and partitioned between AcOEt and aq. HCl (0.5 M). The organic layer was washed with sat. aq. NaHCO$_3$, brine, dried (Na$_2$SO$_4$), and evaporated. The residue was purified by silica gel column chromatography (50% AcOEt in hexane) to give 17 (23 mg, 55%) as a colorless oil. $^1$H NMR (500 MHz, CDCl$_3$) δ 8.03 (br s, 1H, NH), 7.54 (d, 2H, aromatic, J=7.8 Hz), 7.33 (t, 2H, aromatic, J=7.8, 8.2 Hz), 7.13 (t, 1H, aromatic, J=8.2 Hz), 4.51 (m, 2H, CH$_2$CH$_2$O), 2.85 (s, 2H, OC(O)CH$_2$), 2.52 (m, 1H, CH$_2$CH$_2$O), 2.20 (m, 1H, CH$_2$CH$_2$O), 1.64 (s, 3H, CH$_3$); $^{13}$C NMR (125 MHz, CDCl$_3$) δ 166.1, 148.9, 137.4, 129.0, 124.7, 120.1, 82.4, 65.0, 48.4, 30.7, 25.6; HRMS (pos. ion ESI) m/z calcd for (M+Na)⁺ $C_{13}H_{15}NNaO_4$: 272.0899. Found: 272.0894.

Example 16

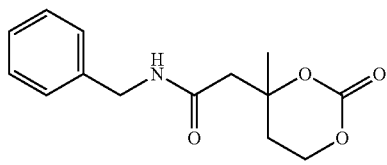

18

18 (27 mg, 61%, colorless oil) was prepared from 8 (29 mg, 0.17 mmol) as described for the preparation of 17 using benzyl amine instead of aniline. ¹H NMR (500 MHz, CDCl₃) δ 7.26-7.35 (m, 5H, aromatic), 6.47 (br s, 1H, NH), 4.38-4.46 (m, 4H, CH₂CH₂O and benzyl-CH₂), 2.68 (d, 1H, OC(O) CH₂, J=14.5 Hz), 2.63 (d, 1H, OC(O)CH₂, J=14.5 Hz), 2.46 (m, 1H, CH₂CH₂O), 2.09 (m, 1H, CH₂CH₂O), 1.55 (s, 3H, CH₃); HRMS (pos. ion ESI) m/z calcd for (M+Na)⁺ $C_{14}H_{17}NNaO_4$: 286.1055. Found: 286.1052.

Example 17

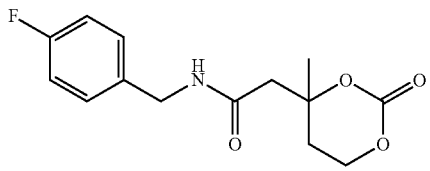 [SMILES: CC1(CC(=O)NCc2ccc(F)cc2)CCOC(=O)O1]

19 (19 mg, 38%, colorless oil) was prepared from 8 (29 mg, 0.17 mmol) as described for the preparation of 17 using 4-fluorobenzyl amine instead of aniline. ¹H NMR (500 MHz, CDCl₃) δ 7.24-7.27 (m, 2H, aromatic), 6.99-7.02 (m, 2H, aromatic), 6.70 (br s, 1H, NH), 4.37-4.44 (m, 4H, CH₂CH₂O and benzyl-CH₂), 2.66 (s, 2H, OC(O)CH₂), 2.45 (m, 1H, CH₂CH₂O), 2.10 (m, 1H, CH₂CH₂O), 1.54 (s, 3H, CH₃); HRMS (pos. ion ESI) m/z calcd for (M+Na)⁺ $C_{14}H_{16}FNNaO_4$: 304.1961. Found: 304.0960.

Example 18

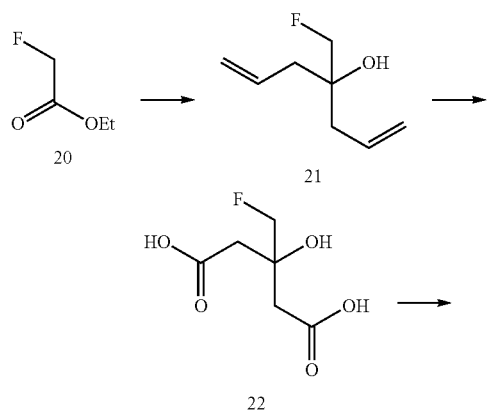

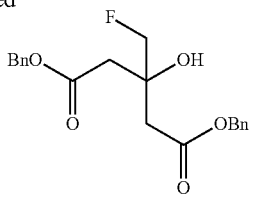

23

To a solution of ethyl fluoroacetate (1.94 mL, 20.0 mmol) in Et₂O (120 mL) was added allylmagnesium bromide (1.0 M solution in Et₂O, 39.0 mL, 39.0 mmol) at 0° C., and the mixture was stirred at 0° C. for 20 min. The reaction was quenched with addition of sat. aq. NH₄Cl, and separated. The organic layer was washed with brine, dried (Na₂SO₄), and evaporated. The residue was used to the next reaction without further purification. The crude product 35 (2.60 g) was dissolved in CH₂Cl₂ (40 mL) and cooled to −78° C. Ozone was bubbled into the solution at −78° C. for 30 min until the color of the solution turned to light purple. Oxygen was bubbled into the solution for 20 min to remove ozone, and the solution was warmed to room temperature. Acetic acid (20 mL) was added to the solution and then the solvent was reduced in vacuo until the amount of the solution was a few milliliters. To the residue were added acetic acid (15 mL), H₂O (15 mL), conc. H₂SO₄ (0.40 mL), and aq. H₂O₂ (30%, 9.0 mL), and the mixture was stirred under reflux for 4 h. After cooling to room temperature, the mixture was neutralized with BaCO₃ (1.5 g) and filtered through Celite with acetone. To the filtrate was added Pd/C (30 mg) and the mixture was stirred at rt for 8 h to decompose H₂O₂. The mixture was filtered through Celite with acetone to remove Pd/C and the filtrate was evaporated. The residue was co-evaporated with H₂O (×2) and toluene (×3) to give the crude of dicarboxylic acid 22 as a brown oil. To a solution of the crude product 22 in DMF (80 mL) were added benzyl bromide (98%, 4.85 mL, 40 mmol) and K₂CO₃ (5.53 g, 40 mmol), and the mixture was stirred at rt for 8 h. After filtration through Celite to remove K₂CO₃, the solvent was evaporated. The residue was partitioned between AcOEt and aq. HCl (0.5 M). The organic layer was washed with sat. aq. NaHCO₃ and brine, dried (Na₂SO₄), and evaporated. The residue was purified by silica gel column chromatography (10% to 20% AcOEt in hexane) to give diester 23 (3.87 g, 54% for 4 steps) as a light yellow oil. ¹H NMR (500 MHz, CDCl₃) δ 7.32-7.38 (m, 10H, aromatic), 5.14 (s, 4H, benzyl-CH₂×2), 4.42 (d, 2H, CH₂F, J=47 Hz), 4.25 (s, 1H, OH), 2.78 (m, 4H, C(O)CH₂×2); ¹³C NMR (125 MHz, CDCl₃) δ 171.0, 135.3, 128.6, 128.5, 128.3, 86.4 (d), 71.1, 66.8, 39.9; HRMS (pos. ion ESI) m/z calcd for (M+Na)⁺ $C_{20}H_{21}FNaO_5$: 383.1271. Found: 383.1276.

Example 19

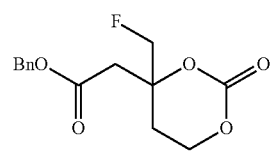

25

To a solution of 23 (280 mg, 0.777 mmol) in THF (8 mL) was added DIBAL-H (1.0 M solution in THF, 0.932 mL, 0.932 mmol) at 0° C., and the mixture was stirred at 0° C. for 10 min. DIBAL-H (1.0 M solution in THF, 1.86 mL, 1.86 mmol) was added to the mixture at 0° C., and the resulting mixture was stirred at 0° C. for 15 min. The reaction was quenched with addition of aq. HCl (1.5 M) that was saturated with NaCl, and extracted with AcOEt. The organic layer was washed with aq. HCl (1.5 M), which was saturated with NaCl, sat. aq. NaHCO$_3$, and brine, and then dried (Na$_2$SO$_4$) and evaporated. After the residue was dissolved in CH$_2$Cl$_2$ (60 mL), pyridine (285 μL, 3.50 mmol) was added to the solution and the mixture was cooled at 0° C. To the mixture was added a solution of triphosgene (98%, 706 mg, 2.33 mmol) in CH$_2$Cl$_2$ (4 mL), and the resulting mixture was stirred at 0° C. for 30 min. The reaction was quenched with addition of sat. aq. NH$_4$Cl, and extracted with AcOEt. The organic layer was washed with brine, dried (Na$_2$SO$_4$), and evaporated. The residue was purified by silica gel column chromatography (33% to 50% AcOEt in hexane) to give 25 (81 mg, 37% for 2 steps) as a colorless oil. $^1$H NMR (500 MHz, CDCl$_3$) δ 7.33-7.40 (m, 5H, aromatic), 5.15 (s, 2H, benzyl-CH$_2$), 4.62 (dd, 1H, CH$_2$F, J=10.0, 12.6 Hz), 4.54 (dd, 1H, CH$_2$F, J=10.0, 12.2 Hz), 4.40 (m, 2H, CH$_2$CH$_2$O), 2.86 (m, 2H, C(O)CH$_2$), 2.37 (m, 1H, CH$_2$CH$_2$O), 2.30 (m, 1H, CH$_2$CH$_2$O); $^{13}$C NMR (125 MHz, CDCl$_3$) δ 168.0, 148.1, 134.9, 128.7, 128.7, 128.5, 85.0 (d), 81.1, 67.2, 64.1, 39.8, 25.9; HRMS (pos. ion ESI) m/z calcd for (M+Na)$^+$ C$_{14}$H$_{15}$FNaO$_5$: 305.0801. Found: 305.0800.

Example 20

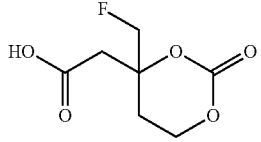

26

26 (249 mg, 99%, colorless oil) was prepared from 25 (368 mg, 1.30 mmol) as described for the preparation of 8. $^1$H NMR (500 MHz, acetone-d$_6$) δ 4.72 (d, 2H, CH$_2$F, J=48 Hz), 4.48 (m, 2H, CH$_2$CH$_2$O), 2.94 (m, 2H, C(O)CH$_2$), 2.47 (m, 1H, CH$_2$CH$_2$O), 2.32 (m, 1H, CH$_2$CH$_2$O); $^{13}$C NMR (125 MHz, acetone-d$_6$) δ 170.6, 148.7, 86.4 (d), 82.3, 64.9, 39.4, 26.4; HRMS (pos. ion ESI) m/z calcd for (M+Na)$^+$ C$_7$H$_9$FNaO$_5$: 215.0332. Found: 215.0330.

Example 21

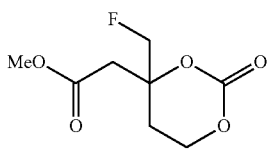

27

27 (32 mg, 60%, white solid) was prepared from 26 (50 mg, 0.26 mmol) as described for the preparation of 12 using NaHCO$_3$ instead of K$_2$CO$_3$. $^1$H NMR (500 MHz, CDCl$_3$) δ 4.60 (d, 2H, CH$_2$F, J=47 Hz), 4.44 (m, 2H, CH$_2$CH$_2$O), 3.73 (s, 3H, OCH$_3$), 2.84 (m, 2H, C(O)CH$_2$), 2.39 (m, 1H, CH$_2$CH$_2$O), 2.32 (m, 1H, CH$_2$CH$_2$O); $^{13}$C NMR (125 MHz, CDCl$_3$) δ 168.7, 148.1, 85.1 (d), 81.1, 64.2, 52.4, 39.7, 26.1; HRMS (pos. ion ESI) m/z calcd for (M+Na)$^+$ C$_8$H$_{11}$FNaO$_5$: 229.0488. Found: 229.0487. mp. 42.0-42.5° C.

Example 22

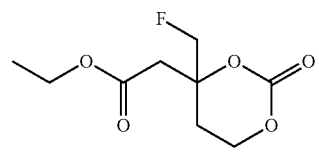

28

28 (31 mg, 58%, colorless oil) was prepared from 26 (46 mg, 0.24 mmol) as described for the preparation of 12 using iodoethane instead of iodomethane. $^1$H NMR (500 MHz, CDCl$_3$) δ 4.60 (d, 2H, CH$_2$F, J=48 Hz), 4.45 (m, 2H, CH$_2$CH$_2$O), 4.18 (q, 2H, CH$_3$CH$_2$O, J=7.2 Hz), 2.82 (m, 2H, C(O)CH$_2$), 2.40 (m, 1H, CH$_2$CH$_2$O), 2.32 (m, 1H, CH$_2$CH$_2$O), 1.29 (t, 3H, CH$_3$CH$_2$O, J=7.2 Hz); $^{13}$C NMR (125 MHz, CDCl$_3$) δ 168.2, 148.2, 85.1 (d), 81.1, 64.2, 39.9, 29.7, 26.0, 14.1; HRMS (pos. ion ESI) m/z calcd for (M+Na)$^+$ C$_9$H$_{13}$FNaO$_5$: 243.0645. Found: 243.0644.

Example 23

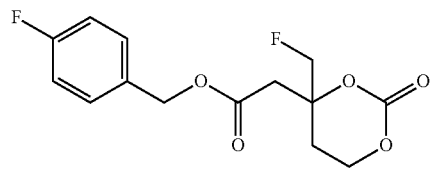

29

29 (41 mg, 77%, colorless oil) was prepared from 26 (34 mg, 0.18 mmol) as described for the preparation of 12 using 4-fluorobenzyl bromide instead of iodomethane. $^1$H NMR (500 MHz, CDCl$_3$) δ 7.33-7.36 (m, 2H, aromatic), 7.05-7.08 (m, 2H, aromatic), 5.12 (s, 2H, benzyl-CH$_2$), 4.61 (dd, 1H, CH$_2$F, J=10.0, 14.0 Hz), 4.52 (dd, 1H, CH$_2$F, J=10.0, 13.6 Hz), 4.42 (m, 2H, CH$_2$CH$_2$O), 2.86 (m, 2H, C(O)CH$_2$), 2.35 (m, 1H, CH$_2$CH$_2$O), 2.28 (m, 1H, CH$_2$CH$_2$O); $^{13}$C NMR (125 MHz, CDCl$_3$) δ 168.0, 162.8 (d), 148.0, 130.8, 130.7, 115.7, 85.0 (d), 81.0, 66.5, 64.1, 40.0, 26.1; HRMS (pos. ion ESI) m/z calcd for (M+Na)$^+$ C$_{14}$H$_{14}$F$_2$NaO$_5$: 323.0707. Found: 323.0707.

Example 24

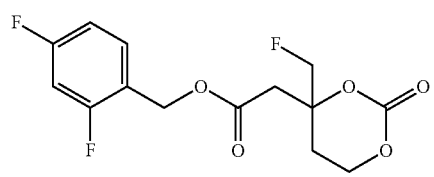

30

30 (36 mg, 72%, colorless oil) was prepared from 26 (30 mg, 0.16 mmol) as described for the preparation of 12 using 2,4-difluorobenzyl bromide instead of iodomethane. $^1$H NMR (500 MHz, CDCl$_3$) δ 7.38 (m, 1H, aromatic), 6.83-6.92 (m, 2H, aromatic), 5.17 (s, 2H, benzyl-CH$_2$), 4.62 (dd, 1H, CH$_2$F, J=10.0, 13.1 Hz), 4.52 (dd, 1H, CH$_2$F, J=10.0, 12.8 Hz), 4.42 (m, 2H, CH$_2$CH$_2$O), 2.85 (m, 2H, C(O)CH$_2$), 2.37 (m, 1H, CH$_2$CH$_2$O), 2.29 (m, 1H, CH$_2$CH$_2$O); $^{13}$C NMR (125 MHz, CDCl$_3$) δ 167.9, 163.4 (d), 161.4 (d), 148.0, 132.2, 118.2, 111.7, 104.2, 85.0 (d), 81.0, 64.2, 60.6, 39.9, 26.0; HRMS (pos. ion ESI) m/z calcd for (M+Na)$^+$ C$_{14}$H$_{13}$F$_3$NaO$_5$: 341.0613. Found: 341.0612.

Example 25

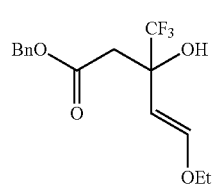

32

To a solution of lithium diisopropylamide (1.8 M solution in heptane/THF/ethyl benzene, 3.05 mL, 5.50 mmol) in THF (55 mL) was added benzyl acetate (784 μL, 5.50 mmol) at −78° C., and the mixture was stirred at −78° C. for 30 min. A solution of 4-ethoxy-1,1,1-trifluoro-3-buten-2-one (712 μL, 5.00 mmol) in THF (5 mL) was added to the mixture via canule at −78° C., and the resulting mixture was stirred at −78° C. for 30 min. After the addition of sat. aq. NH$_4$Cl, the mixture was warmed to room temperature, and evaporated. The residue was partitioned between AcOEt and sat. aq. NH$_4$Cl. The organic layer was washed with brine, dried (Na$_2$SO$_4$), and evaporated. The residue was purified by silica gel column chromatography (6% AcOEt in hexane) to give 32 (1.36 g, 86%) as a light yellow oil. $^1$H NMR (500 MHz, CDCl$_3$) δ 7.33-7.40 (m, 5H, aromatic), 6.74 (d, 1H, CH═CHOEt, J=12.6 Hz), 5.20 (d, 1H, benzyl-CH$_2$, J=14.1 Hz), 5.16 (d, 1H, benzyl-CH$_2$, J=14.1 Hz), 4.76 (s, 1H, OH), 4.71 (d, 1H, CH═CHOEt, J=12.6 Hz), 3.70 (m, 2H, CH$_2$CH$_3$), 2.86 (d, 1H, C(O)CH$_2$, J=15.6 Hz), 2.71 (d, 1H, C(O)CH$_2$, J=15.6 Hz), 1.27 (t, 3H, CH$_2$CH$_3$, J=7.0 Hz); $^{13}$C NMR (125 MHz, CDCl$_3$) δ 171.2, 151.8, 134.8, 128.7, 128.5, 128.3, 124.6 (q), 99.4, 73.3 (q), 67.5, 65.5, 38.9, 14.7; HRMS (pos. ion ESI) m/z calcd for (M+Na)$^+$ C$_{15}$H$_{17}$F$_3$NaO$_4$: 341.0977. Found: 341.0978.

Example 26

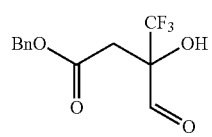

33

To a solution of 32 (334 mg, 1.05 mmol) in acetone (16 mL) was added aq. HCl (12 M, 4 mL) at 0° C., and the mixture was stirred vigorously at 0° C. for 8 min. To the mixture was added sat. aq. NaHCO$_3$ to neutralize, and extracted with AcOEt. The organic layer was washed with sat. aq. NaHCO$_3$ and brine, dried (Na$_2$SO$_4$), and evaporated. The residue was purified by silica gel column chromatography (20% AcOEt in hexane) to give 33 (243 mg, 80%) as a light yellow oil. $^1$H NMR (500 MHz, CDCl$_3$) δ 9.85 (s, 1H, CHO), 7.34-7.40 (m, 5H, aromatic), 5.35 (s, 1H, OH), 5.19 (s, 2H, bezyl-CH$_2$), 2.75-2.93 (m, 4H, CH$_2$CHO and C(O)CH$_2$); $^{13}$C NMR (125 MHz, CDCl$_3$) δ 199.0, 170.8, 134.5, 128.8, 128.7, 128.5, 124.8 (q), 73.3 (q), 67.7, 46.1, 36.9; HRMS (pos. ion ESI) m/z calcd for (M+Na)$^+$ C$_{13}$H$_{13}$F$_3$NaO$_4$: 313.0664. Found: 313.0660.

Example 27

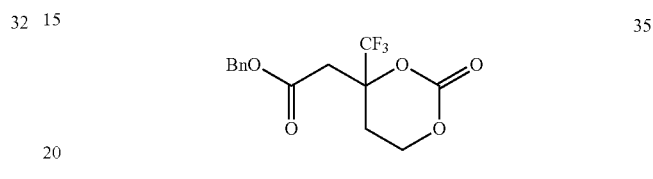

35

To a solution of 33 (320 mg, 1.10 mmol) in benzene (10 mL) was added sodium triacetoxyborohydride (95%, 701 mg, 3.31 mmol) at 0° C., and the mixture was stirred at rt for 2 h. The mixture was quenched with addition of sat. aq. NaHCO$_3$, and extracted with AcOEt. The organic layer was washed with sat. aq. NaHCO$_3$, brine, dried (Na$_2$SO$_4$), and evaporated. After the residue was dissolved in CH$_2$Cl$_2$ (10 mL), pyridine (125 μL, 1.54 mmol) was added to the solution and the mixture was cooled at 0° C. To the mixture was added a solution of triphosgene (98%, 400 mg, 1.32 mmol) in CH$_2$Cl$_2$ (2 mL) at 0° C., and the resulting mixture was stirred at 0° C. for 30 min. The reaction was quenched with addition of sat. aq. NH$_4$Cl, and extracted with AcOEt. The organic layer was washed with brine, dried (Na$_2$SO$_4$), and evaporated. The residue was purified by silica gel column chromatography (33% AcOEt in hexane) to give 35 (281 mg, 80% for 2 steps) as a colorless solid. $^1$H NMR (500 MHz, CDCl$_3$) δ 7.34-7.41 (m, 5H, aromatic), 5.18 (s, 2H, benzyl-CH$_2$), 4.43 (m, 1H, CH$_2$CH$_2$O), 4.37 (m, 1H, CH$_2$CH$_2$O), 3.10 (d, 1H, C(O)CH$_2$, J=16.5 Hz), 2.87 (d, 1H, C(O)CH$_2$, J=16.5 Hz), 2.74 (m, 1H, CH$_2$CH$_2$O), 2.33 (m, 1H, CH$_2$CH$_2$O); $^{13}$C NMR (125 MHz, CDCl$_3$) δ 167.2, 146.8, 134.8, 128.8, 128.7, 128.5, 123.6 (q), 80.2 (q), 67.3, 64.1, 37.9, 24.2; HRMS (pos. ion ESI) m/z calcd for (M+Na)$^+$ C$_{14}$H$_{13}$F$_3$NaO$_5$: 341.0613. Found: 341.0613. mp. 87.5-88° C.

Example 28

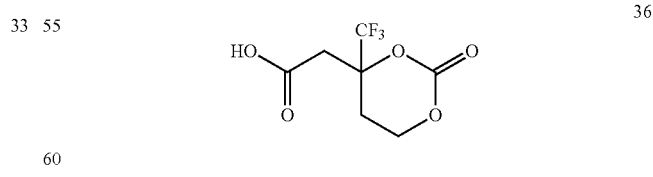

36

36 (176 mg, 98%, colorless oil) was prepared from 35 (250 mg, 0.786 mmol) as described for the preparation of 8. $^1$H NMR (500 MHz, D$_2$O) δ 4.61 (m, 2H, CH$_2$CH$_2$O), 3.22 (d, 1H, C(O)CH$_2$, J=16.5 Hz), 3.12 (d, 1H, C(O)CH$_2$, J=16.5 Hz), 2.76 (m, 1H, CH$_2$CH$_2$O), 2.59 (m, 1H, CH$_2$CH$_2$O); $^{13}$C NMR (125 MHz, D$_2$O) δ 171.4, 150.4, 123.4 (q), 81.1 (q), 65.3, 36.8, 23.5; HRMS (pos. ion ESI) m/z calcd for (M+Na)⁺ $C_7H_7F_3NaO_5$: 251.0143. Found: 251.0140.

Example 29

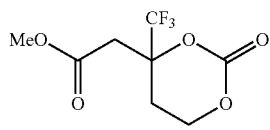

37

Ester 37 (36 mg, 76%, colorless oil) was prepared from 36 (45 mg, 0.20 mmol) as described for the preparation of 27. ¹H NMR (500 MHz, CDCl₃) δ 4.48 (m, 2H, CH₂CH₂O), 3.76 (s, 3H, OCH₃), 3.07 (d, 1H, C(O)CH₂, J=16.4 Hz), 2.86 (d, 1H, C(O)CH₂, J=16.4 Hz), 2.78 (m, 1H, CH₂CH₂O), 2.37 (m, 1H, CH₂CH₂O); ¹³C NMR (125 MHz, CDCl₃) δ 167.7, 146.8, 123.6 (q), 80.1 (q), 64.1, 52.6, 37.5, 24.1; HRMS (pos. ion ESI) m/z calcd for (M+Na)⁺ $C_8H_9F_3NaO_5$: 265.0300. Found: 265.0301.

Example 30

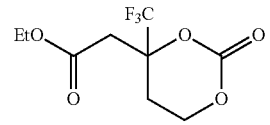

54

Ester 38 (34 mg, 71%, colorless oil) was prepared from 36 (43 mg, 0.19 mmol) as described for the preparation of 27. ¹H NMR (500 MHz, CDCl₃) δ 4.47 (m, 2H, CH₂CH₂O), 4.21 (q, 2H, CH₃CH₂O, J=7.1 Hz), 3.05 (d, 1H, C(O)CH₂, J=16.3 Hz), 2.84 (d, 1H, C(O)CH₂, J=16.3 Hz), 2.78 (m, 1H, CH₂CH₂O), 2.36 (m, 1H, CH₂CH₂O), 1.29 (t, 3H, CH₃CH₂O, J=7.1 Hz); ¹³C NMR (125 MHz, CDCl₃) δ 167.3, 146.8, 123.6 (q), 80.2 (q), 64.2, 61.9, 37.8, 24.2, 14.0; HRMS (pos. ion ESI) m/z calcd for (M+Na)⁺ $C_9H_{11}F_3NaO_5$: 279.0456. Found: 279.0456.

Example 31

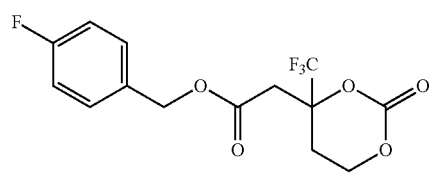

Ester 39 (48 mg, 88%, white solid) was prepared from 36 (39 mg, 0.17 mmol) as described for the preparation of 27. ¹H NMR (500 MHz, CDCl₃) δ 7.35 (m, 2H, aromatic), 7.07 (m, 2H, aromatic), 5.14 (s, 2H, benzyl-CH₂), 4.37-4.47 (m, 2H, CH₂CH₂O), 3.09 (d, 1H, C(O)CH₂, J=16.4 Hz), 2.86 (d, 1H, C(O)CH₂, J=16.4 Hz), 2.73 (m, 1H, CH₂CH₂O), 2.33 (m, 1H, CH₂CH₂O); ¹³C NMR (125 MHz, CDCl₃) δ 167.1, 162.9 (d), 146.7, 130.8, 130.7, 123.6 (q), 115.6, 80.1 (q), 66.8, 64.0, 37.7, 24.1; HRMS (pos. ion ESI) m/z calcd for (M+Na)⁺ $C_{14}H_{12}F_4NaO_5$: 359.0519. Found: 359.0518. mp. 84-85° C.

Example 32

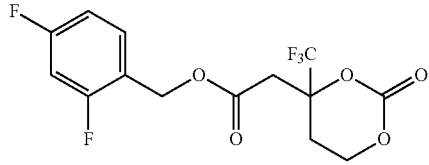

40

Ester 40 (45 mg, 85%, colorless oil) was prepared from 36 (36 mg, 0.16 mmol) as described for the preparation of 27. ¹H NMR (500 MHz, CDCl₃) δ 7.38 (m, 1H, aromatic), 6.88 (m, 2H, aromatic), 5.21 (d, 1H, benzyl-CH₂, J=12.2 Hz), 5.17 (d, 1H, benzyl-CH₂, J=12.2 Hz), 4.45 (m, 2H, CH₂CH₂O), 3.09 (d, 1H, C(O)CH₂, J=16.4 Hz), 2.87 (d, 1H, C(O)CH₂, J=16.4 Hz), 2.75 (m, 1H, CH₂CH₂O), 2.35 (m, 1H, CH₂CH₂O); ¹³C NMR (125 MHz, CDCl₃) δ 167.0, 163.4 (d), 161.4 (d), 146.6, 132.3, 123.5 (q), 118.0, 111.6, 104.2, 80.0 (q), 64.1, 60.9, 37.6, 24.1; HRMS (pos. ion ESI) m/z calcd for (M+Na)⁺ $C_{14}H_{11}F_5NaO_5$: 377.0424. Found: 377.0427.

Example 33

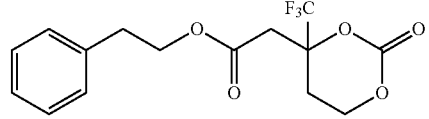

41

Ester 41 (54 mg, 75%, colorless oil) was prepared from 36 (50 mg, 0.22 mmol) as described for the preparation of 27. ¹H NMR (500 MHz, CDCl₃) δ 7.69-7.25 (m, 5H, aromatic), 4.55 (d, 1H), 4.44 (m, 2H), 3.82 (m, 2H), 3.02 (m, 2H), 2.92 (m, 2H), 2.65 (m, 1H); 13C NMR (125 MHz, CDCl3) δ 165.53, 161.86, 141.62 (q), 131.28, 128.87 (d), 126.83, 124.21, 121.70, 66.01 (d), 61.05, 34.88, 29.96, 21.79; MS (pos. ion ESI) m/z calcd for (M+H)⁺ $C_{14}H_{11}F_5O_5$: 333.09. Found: 333.18.

Example 34

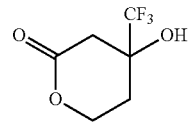

42

To a solution of 33 (267 mg, 0.919 mmol) in benzene (10 mL) was added sodium triacetoxyborohydride (95%, 615 mg, 2.76 mmol) at 0° C., and the mixture was stirred at rt for 2 h. The mixture was quenched with addition of sat. aq. NaHCO₃, and extracted with AcOEt. The organic layer was washed with sat. aq. NaHCO₃, brine, dried (Na₂SO₄), and evaporated. After the residue was dissolved in CH₂Cl₂ (10 mL), trifluoroacetic acid (1 mL) was added to the solution at 0° C., and the mixture was stirred at rt for 2 h. The mixture was diluted with AcOEt and evaporated. The residue was purified by silica gel column chromatography (33% AcOEt in hexane) to give 42 (135 mg, 80% for 2 steps) as a yellow oil. $^1$H NMR (500 MHz, CDCl$_3$) δ 4.61 (m, 1H, CH$_2$CH$_2$O), 4.45 (m, 1H, CH$_2$CH$_2$O), 2.86 (d, 1H, CH$_2$C(O), J=14.7 Hz), 2.84 (br s, 1H, OH), 2.78 (d, 1H, CH$_2$C(O), J=14.7 Hz), 2.24 (m, 1H, CH$_2$CH$_2$O), 2.07 (m, 1H, CH$_2$CH$_2$O); $^{13}$C NMR (125 MHz, CDCl$_3$) δ 167.5, 124.7 (q), 71.5 (q), 64.4, 36.9, 28.6; HRMS (pos. ion ESI) m/z calcd for (M+Na)$^+$ C$_6$H$_7$F$_3$NaO$_3$: 207.0245. Found: 207.0233.

Example 35

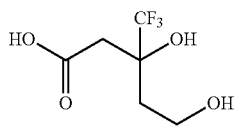

43

To a solution of 42 (10 mg, 0.054 mmol) in H$_2$O (1 mL) was added KOH (≥90%, 3.4 mg, 0.052 mmol) at rt, and the mixture was stirred at 40° C. for 2 h. The pH of the solution was lowered to about pH 7-8 (detected by pH indicator paper) with aq. HCl (0.1 M). The solvent was evaporated and lyophilized to give 43 (15 mg) as a white powder including KCl. $^1$H NMR (500 MHz, D$_2$O) δ 3.79 (m, 2H, CH$_2$CH$_2$O), 2.60 (d, 1H, C(O)CH$_2$, J=15.5 Hz), 2.52 (d, 1H, C(O)CH$_2$, J=15.5 Hz), 2.04 (m, 1H, CH$_2$CH$_2$O), 1.96 (m, 1H, CH$_2$CH$_2$O); $^{13}$C NMR (125 MHz, D$_2$O) δ 178.4, 125.9 (q), 73.2 (q), 56.4, 38.3, 35.9; LRMS (ESI) m/z=225 (M+Na)$^+$.

Example 36

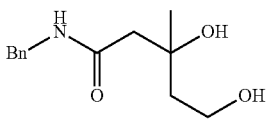

44

(R = H)

To a solution of (±)-mevalonolanctone (97%, 134 mg, 1.00 mmol) in DMF (1 mL) was added benzyl amine (131 μL, 1.20 mmol) at rt, and the mixture was stirred at 80° C. for 12 h. After evaporated, the residue was partitioned between AcOEt and H$_2$O. The organic layer was washed with brine, dried (Na$_2$SO$_4$), and evaporated. The residue (light yellow oil) was used without further purification. LRMS (ESI) m/z=260 (M+Na)$^+$.

Example 37

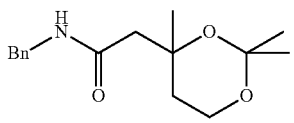

47

To a solution of the crude product 44 (55 mg, ≤0.23 mmol) in CH$_2$Cl$_2$ (2 mL) were added 2,2-dimethoxypropane (112 μL, 0.91 mmol) and camphor sulfonic acid (4 mg, 0.02 mmol) at 0° C. and the mixture was stirred at rt for 16 h. After addition of sat. aq. NaHCO$_3$, the mixture was extracted with AcOEt. The organic layer was washed with brine, dried (Na$_2$SO$_4$), and evaporated. The residue was purified by silica gel column chromatography (50% AcOEt in hexane) to give 47 (17 mg, 27% for 2 steps) as a colorless oil. $^1$H NMR (500 MHz, CDCl$_3$) δ 7.27-7.35 (m, 5H, aromatic), 6.97 (br s, 1H, NH), 4.53 (dd, 1H, benzyl-CH$_2$, J=6.0, 14.8 Hz), 4.39 (dd, 1H, benzyl-CH$_2$, J=5.3, 14.8 Hz), 4.02 (m, 1H, CH$_2$CH$_2$O), 3.83 (m, 1H, CH$_2$CH$_2$O), 2.49 (d, 1H, NHC(O)CH$_2$, J=14.4 Hz), 2.44 (d, 1H, NHC(O)CH$_2$, J=14.4 Hz), 1.91 (m, 1H, CH$_2$CH$_2$O), 1.51 (m, 1H, CH$_2$CH$_2$O), 1.41 (s, 6H, C(CH$_3$)$_2$), 1.23 (s, 3H, CH$_3$); $^{13}$C NMR (125 MHz, CDCl$_3$) δ 170.3, 138.4, 128.6, 127.7, 127.4, 98.5, 72.0, 56.5, 51.1, 43.4, 33.3, 29.9, 26.7, 25.7; HRMS (pos. ion ESI) m/z calcd for (M+Na)$^+$ C$_{16}$H$_{23}$NNaO$_3$: 300.1576. Found: 300.1586.

Example 38

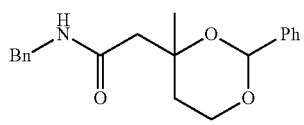

49

(A major diastereomer)

To a solution of the crude product 44 (54 mg, ≤0.23 mmol) in CH$_2$Cl$_2$ (2 mL) were added benzaldehyde demethyl acetal (51 μL, 0.34 mmol) and camphor sulfonic acid (4 mg, 0.02 mmol) at 0° C. and the mixture was stirred at rt for 16 h. After addition of sat. aq. NaHCO$_3$, the mixture was extracted with AcOEt. The organic layer was washed with brine, dried (Na$_2$SO$_4$), and evaporated. The residue was purified by silica gel column chromatography (33-50% AcOEt in hexane) to give 49 (25 mg, 34% for 2 steps) as a white solid. $^1$H NMR (500 MHz, CDCl$_3$) δ 7.20-7.32 (m, 10H, aromatic), 6.83 (br s, 1H, NH), 5.72 (s, 1H, benzyl-CH), 4.47 (dd, 1H, benzyl-CH$_2$, J=5.8, 14.6 Hz), 4.38 (dd, 1H, benzyl-CH$_2$, J=5.3, 14.6 Hz), 4.14 (m, 2H, CH$_2$CH$_2$O), 2.55 (s, 2H, NHC(O)CH$_2$), 2.16 (m, 1H, CH$_2$CH$_2$O), 1.53 (s, 3H, CH$_3$), 1.46 (m, 1H, CH$_2$CH$_2$O); $^{13}$C NMR (125 MHz, CDCl$_3$) δ 169.7, 138.3, 138.1, 128.9, 128.7, 128.4, 127.9, 127.4, 125.8, 95.3, 73.4, 63.2, 50.8, 43.6, 33.6, 20.3; HRMS (pos. ion ESI) m/z calcd for (M+Na)$^+$ C$_{20}$H$_{23}$NNaO$_3$: 348.1576. Found: 348.1569.

Example 39

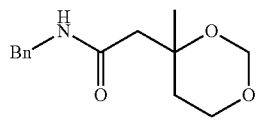

45

To a solution of the crude product 44 (26 mg, ≤0.11 mmol) in CH$_2$Cl$_2$ were added chloromethyl methyl ether (84 μL, 1.1 mmol), N,N-diisopropylethylamine (383 μL, 2.2 mmol), and DMAP (1.2 mg) at 0° C. and the mixture was stirred at rt for 2 h. After dilution with AcOEt, the mixture was partitioned between AcOEt and 0.5 M aq. HCl. The organic layer was washed with sat. aq. NaHCO3, brine, dried (Na2SO4), and evaporated. The residue was dissolved in CH2Cl2 (17 mL), and BF3.Et2O (30 μL, 0.24 mmol) was added at 0° C. The mixture was stirred at rt for 8 h. After addition of sat. aq. NaHCO3, the mixture was extracted with AcOEt. The organic layer was washed with brine, dried (Na2SO4), and evaporated. The residue was purified by silica gel column chromatography (50% AcOEt in hexane) to give 45 (21 mg, 77% for 3 steps) as a white solid. 1H NMR (500 MHz, CDCl3) δ 7.25-7.35 (m, 5H, aromatic), 6.80 (br s, 1H, NH), 4.92 (d, 1H, OCH2O, J=6.5 Hz), 4.85 (d, 1H, OCH2O, J=6.5 Hz), 4.48 (d, 2H, benzyl-CH2, J=5.5 Hz), 3.95 (m, 1H, CH2CH2O), 3.89 (m, 1H, CH2CH2O), 2.60 (d, 1H, NHC(O)CH2, J=14.5 Hz), 2.47 (d, 1H, NHC(O)CH2, J=14.5 Hz), 2.02 (m, 1H, CH2CH2O), 1.48 (m, 1H, CH2CH2O), 1.40 (s, 3H, CH3); $^{13}$C NMR (125 MHz, CDCl3) δ 169.8, 138.5, 128.6, 127.5, 127.3, 87.8, 72.1, 62.8, 49.0, 43.3, 34.7, 20.9; HRMS (pos. ion ESI) m/z calcd for (M+Na)$^+$ C$_{14}$H$_{19}$NNaO$_3$: 272.1263. Found: 272.1259.

Example 40

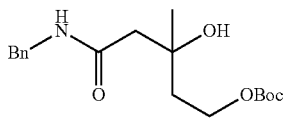

54

To a solution of the crude product 44 (24 mg, ≤0.10 mmol) in acetonitrile (1 mL) were added (Boc)$_2$O (99 mg, 0.45 mmol) and DMAP (1.2 mg, 0.01 mmol) at rt and the mixture was stirred under reflux conditions for 16 h. After evaporated, the residue was purified by silica gel column chromatography (50% AcOEt in hexane) to give 54 (30 mg, 88% for 2 steps) as a colorless oil. $^1$H NMR (500 MHz, CDCl$_3$) δ 7.27-7.36 (m, 5H, aromatic), 6.23 (br s, 1H, NH), 4.65 (s, 1H, OH), 4.46 (m, 2H, benzyl-CH$_2$), 4.22 (m, 2H, CH$_2$CH$_2$O), 2.45 (d, 1H, NHC(O)CH$_2$, J=14.5 Hz), 2.34 (d, 1H, NHC(O)CH$_2$, J=14.5 Hz), 1.90 (t, 2H, CH$_2$CH$_2$O, J=6.8 Hz), 1.45 (s, 9H, C(CH$_3$)$_3$), 1.28 (s, 3H, CH$_3$); HRMS (pos. ion ESI) m/z calcd for (M+Na)$^+$ C$_{18}$H$_{27}$NNaO$_5$: 360.1787. Found: 360.1785.

Example 41

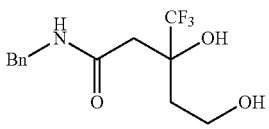

44

To a solution of 41 (120 mg, 0.652 mmol) in DMF was added benzyl amine (142 μL, 1.30 mmol), and the mixture was stirred at 80° C. for 12 h. After the solvent was evaporated, the residue was purified by silica gel column chromatography (50-100% AcOEt in hexane) to give 44 (189 mg, 99%) as a colorless oil: $^1$H NMR (500 MHz, CDCl$_3$) δ 7.34-7.37 (m, 2H, aromatic), 7.26-7.32 (m, 3H, aromatic), 6.62 (s, 1H, OH), 6.29 (br s, 1H, NH), 4.49 (dd, 1H, benzyl-CH$_2$, J=6.0, 14.5 Hz), 4.43 (dd, 1H, benzyl-CH$_2$, J=5.5, 14.5 Hz), 3.95 (m, 1H, CH$_2$CH$_2$O), 3.89 (m, 1H, CH$_2$CH$_2$O), 2.73 (d, 1H, NHC(O)CH$_2$, J=14.7 Hz), 2.51 (m, 1H, OH), 2.49 (d, 1H, NHC(O)CH$_2$, J=14.7 Hz), 2.09 (m, 1H, CH$_2$CH$_2$O), 1.84 (m, 1H, CH$_2$CH$_2$O); $^{13}$C NMR (125 MHz, CDCl$_3$) δ 170.6, 137.2, 128.9, 128.7, 127.9, 125.7 (q), 75.0 (q), 58.4, 43.7, 38.0, 35.3; HRMS (pos. ion ESI) m/z calcd for (M+Na)$^+$ C$_{13}$H$_{16}$F$_3$NNaO$_3$: 314.0980. Found: 314.0991.

Example 42

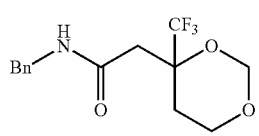

46

46 (26 mg, 69% for 2 steps, colorless oil) was prepared from 44 (36 mg, 0.12 mmol) as described for the preparation of 45. $^1$H NMR (500 MHz, CDCl$_3$) δ 7.27-7.36 (m, 5H, aromatic), 6.43 (br s, 1H, NH), 5.06 (d, 1H, OCH$_2$O, J=6.3 Hz), 4.94 (d, 1H, OCH$_2$O, J=6.3 Hz), 4.55 (dd, 1H, benzyl-CH$_2$, J=6.1, 14.9 Hz), 4.42 (dd, 1H, benzyl-CH$_2$, J=6.0, 14.9 Hz), 3.99 (m, 2H, CH$_2$CH$_2$O), 2.76 (d, 1H, NHC(O)CH$_2$, J=14.4 Hz), 2.56 (d, 1H, NHC(O)CH$_2$, J=14.4 Hz), 2.37 (m, 1H, CH$_2$CH$_2$O), 1.98 (dt, 1H, CH$_2$CH$_2$O, J=3.7, 3.7, 14.7 Hz); $^{13}$C NMR (125 MHz, CDCl$_3$) δ 167.4, 137.9, 129.1, 128.7, 128.6, 128.0, 127.5, 125.7 (q), 89.9, 73.4 (q), 62.5, 43.8, 41.2, 25.7; HRMS (pos. ion ESI) m/z calcd for (M+Na)$^+$ C$_{14}$H$_{16}$F$_3$NNaO$_3$: 326.0980. Found: 326.0970.

Example 43

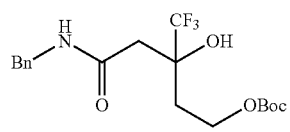

55

55 (50 mg, 68%, colorless oil) were prepared from 44 (55 mg, 0.19 mmol) as described for the preparation of 54. $^1$H NMR (500 MHz, CDCl$_3$) δ 7.26-7.38 (m, 5H, aromatic), 6.55 (s, 1H, OH), 6.05 (br s, 1H, NH), 4.53 (dd, 1H, benzyl-CH$_2$, J=6.0, 14.7 Hz), 4.42 (dd, 1H, benzyl-CH$_2$, J=5.5, 14.7 Hz), 4.29 (m, 2H, CH$_2$CH$_2$O), 2.69 (d, 1H, NHC(O)CH$_2$, J=15.3 Hz), 2.50 (d, 1H, NHC(O)CH$_2$, J=15.3 Hz), 2.15 (m, 1H, CH$_2$CH$_2$O), 1.99 (m, 1H, CH$_2$CH$_2$O), 1.47 (s, 9H, C(CH$_3$)$_3$); $^{13}$C NMR (125 MHz, CDCl$_3$) δ 170.8, 153.1, 137.0, 128.9, 127.9, 127.6, 125.6 (q), 82.5, 73.7 (q), 61.8, 43.8, 37.1, 33.6, 27.7; HRMS (pos. ion ESI) m/z calcd for (M+Na)$^+$ C$_{18}$H$_{24}$F$_3$NNaO$_5$: 414.1504. Found: 414.1500.

Example 44

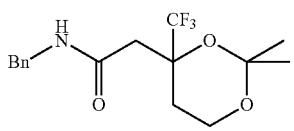

48

48 (20 mg, 32%, colorless oil) were prepared from 44 (55 mg, 0.19 mmol) as described for the preparation of 47. HRMS (pos. ion ESI) m/z calcd for (M+Na)$^+$ C$_{16}$H$_{20}$F$_3$NNaO$_3$: 354.1293. Found: 354.1290.

Example 45

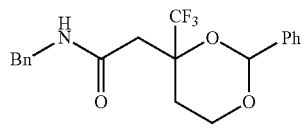

50

To a solution of 44 (60 mg, 0.20 mmol) in CH$_2$Cl$_2$ (2 mL) were added benzaldehyde dimethyl acetal (151 µL, 1.00 mmol) and camphor sulfonic acid (4.7 mg, 0.02 mmol) at rt and the mixture was stirred under reflux condition for 12 h. After addition of sat. aq. NaHCO$_3$, the mixture was extracted with AcOEt. The organic layer was washed with brine, dried (Na$_2$SO$_4$), and evaporated. The residue was purified by silica gel column chromatography (10-25% AcOEt in hexane) to give 50a (25 mg, 33%, CF$_3$/Ph=anti) as a colorless oil or 50b (7 mg, 9%, CF$_3$/Ph=syn) as a white solid. 50a $^1$H NMR (500 MHz, CDCl$_3$) δ 7.25-7.35 (m, 8H, aromatic), 7.16-7.18 (m, 2H, aromatic), 6.46 (br s, 1H, NH), 5.92 (s, 1H, benzylidene-CH), 4.41 (d, 2H, benzyl-CH$_2$, J=5.6 Hz), 4.18 (m, 2H, CH$_2$CH$_2$O), 2.73 (d, 1H, NHC(O)CH$_2$, J=14.3 Hz), 2.57 (d, 1H, NHC(O)CH$_2$, J=14.3 Hz), 2.50 (m, 1H, CH$_2$CH$_2$O), 1.97 (m, 1H, CH$_2$CH$_2$O); $^{13}$C NMR (125 MHz, CDCl$_3$) δ 167.3, 137.5, 129.4, 128.7, 128.5, 128.0, 127.5, 125.5 (q), 98.0, 74.7 (q), 63.2, 43.9, 42.8, 25.0; HRMS (pos. ion ESI) m/z calcd for (M+Na)$^+$ C$_{20}$H$_{20}$F$_3$NNaO$_3$: 402.1293. Found: 412.1285. 50b $^1$H NMR (500 MHz, CDCl$_3$) δ 7.27-7.38 (m, 8H, aromatic), 7.21-7.23 (m, 2H, aromatic), 6.29 (br s, 1H, NH), 5.78 (s, 1H, benzylidene-CH), 4.49 (dd, 1H, benzyl-CH$_2$, J=5.9, 14.6 Hz), 4.36 (dd, 1H, benzyl-CH$_2$, J=5.3, 14.6 Hz), 4.27 (m, 1H, CH$_2$CH$_2$O), 4.19 (m, 1H, CH$_2$CH$_2$O), 3.01 (d, 1H, NHC(O)CH$_2$, J=15.2 Hz), 2.94 (d, 1H, NHC(O)CH$_2$, J=15.2 Hz), 2.36 (m, 1H, CH$_2$CH$_2$O), 2.02 (m, 1H, CH$_2$CH$_2$O); $^{13}$C NMR (125 MHz, CDCl$_3$) δ 167.2, 137.5, 137.0, 129.4, 128.8, 128.4, 127.9, 127.7, 125.9 (q), 96.4, 76.0 (q), 62.5, 44.0, 36.6, 25.5; HRMS (pos. ion ESI) m/z calcd for (M+Na)$^+$ C$_{20}$H$_{20}$F$_3$NNaO$_3$: 402.1293. Found: 412.1283.

Example 46

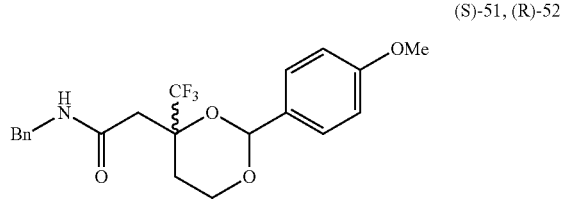 [SMILES: COc1ccc(C2OCCC(CC(=O)NCc3ccccc3)(C(F)(F)F)O2)cc1]

(S)-51, (R)-52

51 (30 mg, 35%, white solid, CF3/PMB=anti) and 52 (22 mg, 25%, colorless oil, CF3/PMB=syn) were prepared from 44 (62 mg, 0.21 mmol) as described for the preparation of 71 using anisaldehyde dimethylacetal instead of benzaldehyde demethyl acetal: 51 $^1$H NMR (500 MHz, CDCl$_3$) δ 7.27-7.31 (m, 3H, aromatic), 7.17-7.20 (m, 4H, aromatic), 6.75 (d, 2H, aromatic, J=8.8 Hz), 6.50 (br s, 1H, NH), 5.86 (s, 1H, benzylidene-CH), 4.42 (d, 2H, benzyl-CH$_2$, J=5.6 Hz), 4.15 (m, 2H, CH$_2$CH$_2$O), 3.79 (s, 3H, OCH$_3$), 2.73 (d, 1H, NHC(O) CH$_2$, J=14.4 Hz), 2.56 (d, 1H, NHC(O)CH$_2$, J=14.4 Hz), 2.46 (m, 1H, CH$_2$CH$_2$O), 1.96 (m, 1H, CH$_2$CH$_2$O); $^{13}$C NMR (125 MHz, CDCl$_3$) δ 167.4, 160.2, 137.6, 129.8, 128.7, 128.1, 127.5, 125.5 (q), 113.8, 97.9, 74.7 (q), 63.2, 55.3, 43.9, 42.8, 25.0; HRMS (pos. ion ESI) m/z calcd for (M+Na)$^+$ C$_{21}$H$_{22}$F$_3$NNaO$_4$: 432.1399. Found: 432.1408. 52 $^1$H NMR (500 MHz, CDCl$_3$) δ 7.28-7.30 (m, 5H, aromatic), 7.22 (m, 2H, aromatic), 6.84 (d, 2H, aromatic, J=8.8 Hz), 6.30 (br s, 1H, NH), 5.73 (s, 1H, benzylidene-CH), 4.51 (dd, 1H, benzyl-CH$_2$, J=6.0, 14.6 Hz), 4.35 (dd, 1H, benzyl-CH$_2$, J=5.2, 14.6 Hz), 4.25 (m, 1H, CH$_2$CH$_2$O), 4.17 (m, 1H, CH$_2$CH$_2$O), 3.80 (s, 3H, OCH$_3$), 2.99 (d, 1H, NHC(O)CH$_2$, J=15.3 Hz), 2.95 (d, 1H, NHC(O)CH$_2$, J=15.3 Hz), 2.34 (m, 1H, CH$_2$CH$_2$O), 1.98 (m, 1H, CH$_2$CH$_2$O); $^{13}$C NMR (125 MHz, CDCl$_3$) δ 167.2, 160.3, 137.5, 129.4, 128.8, 127.9, 127.6, 124.9 (q), 113.8, 96.3, 76.1 (q), 62.5, 55.3, 44.0, 36.5, 25.5; HRMS (pos. ion ESI) m/z calcd for (M+Na)$^+$ C$_{21}$H$_{22}$F$_3$NNaO$_4$: 432.1399. Found: 432.1389.

Example 47

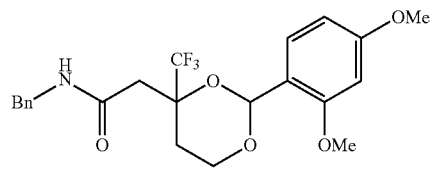

53

To a solution of 44 (74 mg, 0.25 mmol) in benzene (3 mL) were added 2,4-dimethoxybenzaldehyde (98%, 52 mg, 0.31 mmol), camphor sulfonic acid (4.7 mg, 0.02 mmol), and molecular serves 4 A (powder, 18 mg) at rt and the mixture was stirred under reflux condition for 36 h. After addition of sat. aq. NaHCO$_3$, the mixture was extracted with AcOEt. The organic layer was washed with brine, dried (Na$_2$SO$_4$), and evaporated. The residue was purified by preparative TLC (50% AcOEt in hexane×2) to give 53 (7 mg, 6%) as a colorless oil. $^1$H NMR (500 MHz, CDCl$_3$) δ 7.52 (d, 1H, aromatic, J=8.5 Hz), 7.24-7.26 (m, 3H, aromatic), 7.17-7.19 (m, 2H, aromatic), 6.57 (br s, 1H, NH), 6.52 (d, 1H, aromatic, J=8.5 Hz), 6.32 (s, 1H, aromatic), 6.10 (s, 1H, benzylidene-CH), 4.44 (d, 2H, benzyl-CH$_2$, J=5.4 Hz), 4.24 (m, 1H, CH$_2$CH$_2$O), 4.14 (m, 1H, CH$_2$CH$_2$O), 3.80 (s, 3H, OCH$_3$), 3.57 (s, 3H, OCH$_3$), 3.12 (d, 1H, NHC(O)CH$_2$, J=15.3 Hz), 2.90 (d, 1H, NHC(O)CH$_2$, J=15.3 Hz), 2.28 (m, 1H, CH$_2$CH$_2$O), 1.88 (m, 1H, CH$_2$CH$_2$O); $^{13}$C NMR (125 MHz, CDCl$_3$) δ 167.7, 161.7, 157.3, 137.7, 129.4, 128.6, 128.4, 127.5, 127.3, 124.6 (q), 117.9, 104.9, 98.2, 91.1, 76.1 (q), 62.8, 55.4, 43.9, 36.6, 26.0; HRMS (pos. ion ESI) m/z calcd for (M+Na)+ $C_{22}H_{24}F_3NNaO_5$: 462.1504. Found: 462.1503.

Example 48

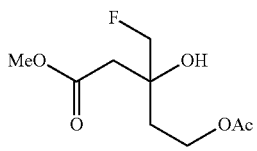

63

To a solution of 23 (500 mg, 1.39 mmol) in THF (10 mL) was added LiBH$_4$ (0.067 g, 3.08 mmol) at 0° C., and the mixture was stirred at 0° C. for 30 min. The reaction was quenched with addition of aq. HCl (1.5 M). The solution was co-evaporated with toluene and the product was extracted from the dry slurry with THF and the solvent was evaporated. The residue (250 mg, 1.64 mmol) was dissolved in THF (5 mL) and stirred with pyridine (0.132 mL, 1.64 mmol) and acetic anhydride (0.24 mL, 2.46 mmol) at room temperature for 8 h. The reaction was quenched with aq. HCl (1.5 M), and extracted with AcOEt. The organic layer was washed with aq. HCl (1.5 M), sat. NaHCO$_3$, and brine, and then dried (MgSO$_4$) and evaporated. The residue was purified by silica gel column chromatography (50% to 75% AcOEt in hexane) to give 61 (239 mg, 75%) as a colorless oil. $^1$H NMR (500 MHz, CDCl$_3$) δ 4.40 (dd, 1H, CHHF, J=9.4, 16.5 Hz), 4.29 (m, 3H), 3.94 (m, 2H), 2.06 (s, 3H), 1.97 (m, 2H), 1.85 (m, 2H); $^{13}$C NMR (125 MHz, CDCl$_3$) δ 171.0, 87.3, 85.9, 73.2 (d), 60.3, 59.3, 36.8, 35.6, 21.1. To a solution of 61 (330 mg, 1.54 mmol) in DMF (5 mL), K$_2$CO$_3$ (638 mg, 4.62 mmol) was added to the mixture followed by the addition of methyl iodide (0.21 mL, 3.08 mmol) and the mixture was stirred for 24 h. The reaction was quenched with aq. HCl (1.5 M) and extracted with ethyl acetate. The organic layer was washed with aq. HCl (1.5 M) and brine, dried (MgSO$_4$) and evaporated. The residue was purified by silica gel column chromatography (15% to 25% EtOAc in hexane) to give 63 (105 mg, 31%). $^1$H NMR (500 MHz, CDCl$_3$) δ 4.41 (dd, 1H, J=9.91 Hz) 4.33-4.24 (m, 3H), 3.92 (s, 1H), 2.72-2.62 (dq, 2H), 2.07 (s, 3H), 1.95 (dt, 2H). $^{13}$C NMR (125 MHz, CDCl$_3$) δ 172.7, 170.9, 87.3, 85.9, 71.2, (d), 59.7, 52.1, 39.5 (d), 35.2, 21.0; HRMS (pos. ion ESI) m/z calcd for (M+Na)+ $C_9H_{15}FO_5$: 245.0801. Found: 245.0933.

Example 49

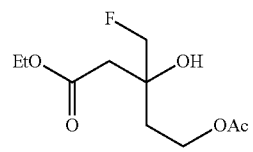

64

To a solution of 62 (300 mg, 1.54 mmol) in DMF (8 mL) was added pyridinium dichromate at room temperature and the mixture was stirred at room temperature for 24 h. The reaction was quenched with aq. HCl (1.5 M) and extracted with AcOEt. The organic layer was washed with aq. HCl (1.5 M) and brine, then dried (MgSO$_4$) and evaporated. After the residue was dissolved in DMF (5 mL), K$_2$CO$_3$ (638 mg, 4.62 mmol) was added to the mixture followed by the addition of methyl iodide (0.21 mL, 3.08 mmol) and the mixture was stirred for 24 h. The reaction was quenched with aq. HCl (1.5 M) and extracted with AcOEt. The organic layer was washed with aq. HCl (1.5 M) and brine, dried (MgSO$_4$) and evaporated. The residue was purified by silica gel column chromatography (15% to 25% AcOEt in hexane) to give 64 (40 mg, 11%) as a colorless oil. $^1$H NMR (500 MHz, CDCl$_3$) δ 4.37 (dd, 1H), 4.30-4.23 (m, 3H), 4.19 (q, 2H, J=7.19), 3.99 (s, 1H), 2.62 (dq, 2H), 2.04 (s, 3H), 1.93 (m, 2H), 1.28 (t, 3H, J=7.19 Hz); $^{13}$C NMR (125 MHz, CDCl$_3$) δ 172.4, 170.9, 87.3, 85.9, 71.2, 61.2, 59.8, 39.7 (d), 35.2 (d), 21.0, 14.1; HRMS (pos. ion ESI) m/z calcd for (M+Na)+ $C_{10}H_{17}FO_5$: 259.0957. Found: 259.1080.

Example 50

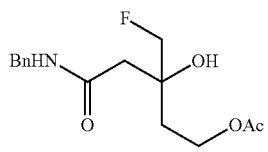

65

To a solution of 43 (R=CH$_2$F, 200 mg, 1.35 mmol) in DMF (5 mL) was added benzylamine (0.18 mL, 1.62 mmol) at room temperature and the reaction was stirred at 60° C. for 24 h. The reaction was quenched by aq. HCl (1.5 M) and extracted with AcOEt. The organic layer was washed with aq. HCl (1.5 M) and brine, then dried (MgSO$_4$) and evaporated. After the residue was dissolved in THF, pyridine (0.11 mL, 1.35 mmol) was added at room temperature. To the solution was added acetic anhydride (0.25 mL, 2.7 mmol) and the mixture was stirred at room temperature for 24 h. The reaction was quenched with aq. HCl (1.5 M) and extracted with AcOEt. The organic layer was washed with aq. HCl (1.5 M) and brine, then dried (MgSO$_4$) and evaporated. The residue was purified by silica gel column chromatography (15% to 25% AcOEt in hexane) to give 65 as a colorless oil. $^1$H NMR (500 MHz, CDCl$_3$) δ 7.24 (m, 5H), 6.03 (s, 1H), 4.98 (s, 1H), 4.43-4.35 (m, 2H), 4.25 (s, 1H), 4.24-4.17 (m, 2H), 4.16 (s, 1H), 2.41 (m, 2H), 1.96 (s, 3H), 1.87-1.84 (m, 2H); $^{13}$C NMR (125 MHz, CDCl$_3$) δ 171.5, 170.9, 137.4, 128.9, 127.8, 87.1, 85.7, 71.3, 59.8, 43.6, 40.7, 35.8, 21.0, HRMS (pos. ion ESI) m/z calcd for (M+Na)+ $C_{15}H_{20}FNO_4$: 320.1274. Found: 320.1268.

We claim:
1. A compound of a formula

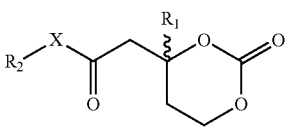

wherein X is selected from NH, O and S; R$_1$ is selected from mono- and polyfluoro-substituted methyl moieties; and R$_2$ is selected from alkyl, mono- and polyfluoro-substituted alkyl, alkanoyloxy, cycloalkyl, mono- and polyfluoro-substituted cycloalkyl, aryl, mono- and polyfluoro-substituted aryl, arylalkyl, and mono- and polyfluoro-substituted arylalkyl moieties.

2. The compound of claim 1 wherein X is selected from NH and O; and $R_1$ is selected from fluoromethyl and trifluoromethyl moieties.

3. The compound of claim 2 wherein $R_2$ is selected from mono- and polyfluoro-substituted arylalkyl moieties.

4. The compound of claim 3 wherein $R_2$ is selected from mono- and difluoro-substituted benzyl moieties.

5. The compound of claim 1 in at least one of human plasma and contact with an enzyme in a streptococcal mevalonate biosynthetic pathway.

6. A compound of a formula

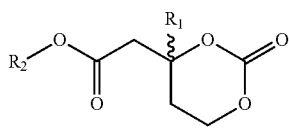

wherein X is selected from NH, O and S; $R_1$ is selected from mono- and polyfluoro-substituted methyl moieties; and $R_2$ is selected from alkyl, mono- and polyfluoro-substituted alkyl, aryl, mono- and polyfluoro-substituted aryl, arylalkyl, and mono- and polyfluoro-substituted arylalkyl moieties.

7. The compound of claim 6 wherein X is selected from NH and O; and $R_1$ is selected from fluoromethyl and trifluoromethyl moieties.

8. The compound of claim 7 wherein $R_2$ is selected from aryl, mono- and polyfluoroaryl, arylalkyl, mono- and polyfluoroarylalkyl moieties.

9. The compound of claim 8 wherein $R_2$ is selected from phenyl, mono- and polyfluorophenyl, benzyl, monofluorobenzyl and polyfluorobenzyl moieties.

10. A compound of a formula

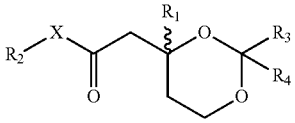

wherein X is selected from NH, O and S; $R_1$ is selected from mono- and polyfluoro-substituted methyl moieties; and $R_2$ is selected from alkyl, mono- and polyfluoro-substituted alkyl, aryl, mono- and polyfluoro-substituted aryl, arylalkyl, mono- and polyfluoro-substituted arylalkyl moieties; and $R_3$ and $R_4$ are independently selected from H, alkyl, $C_1$-$C_2$ alkoxyalkyl, aryl and arylalkyl moieties.

11. The compound of claim 10 wherein X is selected from NH and O; and $R_1$ is independently selected from fluoromethyl and trifluoromethyl moieties.

12. The compound of claim 11 where $R_2$ is selected from arylalkyl, mono- and polyfluoro-substituted arylalkyl moieties.

13. The compound of claim 10 wherein $R_3$ and $R_4$ are independently selected from H and alkyl moieties.

14. The compound of claim 13 wherein at least one of $R_3$ and $R_4$ is methyl.

15. A compound of a formula

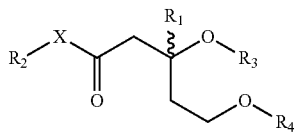

wherein X is selected from NH, O and S; $R_1$ is selected from mono- and polyfluoro-substituted methyl moieties; $R_2$ is selected from alkyl, mono- and polyfluoro-substituted alkyl, aryl, mono- and polyfluoro-substituted aryl, arylalkyl, mono- and polyfluoro-substituted arylalkyl moieties; and $R_3$ and $R_4$ are independently selected from H, acetyl, propionyl and $C_1$-$C_2$ alkoxyalkyl moieties, providing compound is not

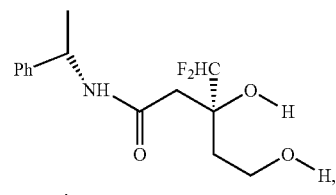

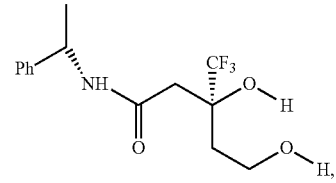

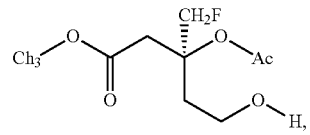

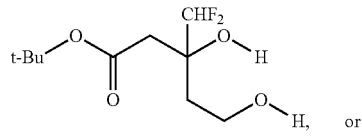

, or

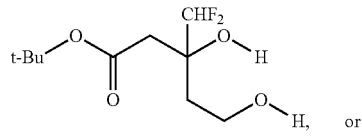

16. The compound of claim 15 wherein X is selected from NH and O; and $R_1$ is selected from fluoromethyl and trifluoromethyl moieties.

17. The compound of claim 16 wherein $R_2$ is selected from alkyl, mono- and polyfluoro-substituted alkyl, aryl, mono- and polyfluoro-substituted aryl, arylalkyl, mono- and polyfluoro-substituted arylalkyl moieties.

18. The compound of claim 15 wherein X is O; $R_2$ is selected from alkyl, aryl and arylalkyl moieties; and $R_3$ and $R_4$ are independently selected from H and acetyl moieties.

19. The compound of claim 18 wherein at least one of $R_3$ and $R_4$ is acetyl.

20. A compound of a formula

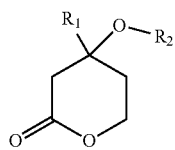

wherein $R_1$ is selected from mono- and polyfluoro-substituted methyl moieties; and $R_2$ is selected from acetyl, propionyl and $C_1$-$C_2$ alkoxyalkyl moieties, providing said compound is not

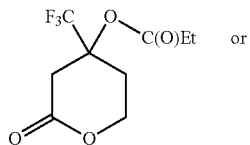 or

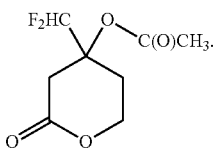

21. The compound of claim 20 wherein $R_1$ is selected from fluoromethyl and trifluoromethyl moieties.

22. The compound of claim 21 wherein $R_2$ is selected from acetyl and propionyl moieties.

23. The compound of claim 22 wherein $R_2$ is acetyl.

* * * * *